US009149277B2

(12) United States Patent
Rudakov et al.

(10) Patent No.: US 9,149,277 B2
(45) Date of Patent: Oct. 6, 2015

(54) EXPANDABLE DEVICE DELIVERY

(75) Inventors: Leon Rudakov, San Marcos, CA (US); Andrew R. Leopold, Hawthorn Woods, IL (US); Kelly L. Jensen, Palatine, IL (US); Philippe Gailloud, Baltimore, MD (US)

(73) Assignee: Artventive Medical Group, Inc., San Marcos, CA (US)

( * ) Notice: Subject to any disclaimer, the term of this patent is extended or adjusted under 35 U.S.C. 154(b) by 1100 days.

(21) Appl. No.: 12/906,993

(22) Filed: Oct. 18, 2010

(65) Prior Publication Data
US 2012/0095489 A1 Apr. 19, 2012

(51) Int. Cl.
*A61F 2/95* (2013.01)
*A61B 17/12* (2006.01)

(52) U.S. Cl.
CPC ....... *A61B 17/12031* (2013.01); *A61B 17/1214* (2013.01); *A61B 17/1215* (2013.01); *A61B 17/12109* (2013.01); *A61B 2017/12054* (2013.01)

(58) Field of Classification Search
CPC ..... A61F 2/06; A61F 2/88; A61F 2002/9505; A61F 2/95; A61B 17/12022; A61B 17/12027; A61B 17/12113; A61B 17/12036; A61B 2017/12054; A61B 2017/12095; A61B 17/1214
USPC .................... 623/1.11, 1.12, 1.14, 1.22, 1.23; 606/108, 191, 198, 195
See application file for complete search history.

(56) References Cited

U.S. PATENT DOCUMENTS

| 3,805,767 | A | 4/1974 | Erb |
| 3,868,956 | A | 3/1975 | Alfidi et al. |
| 3,918,431 | A | 11/1975 | Sinnreich |

(Continued)

FOREIGN PATENT DOCUMENTS

| CN | 2527227 Y | 12/2002 |
| EP | 1166721 A2 | 1/2002 |

(Continued)

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.

(Continued)

*Primary Examiner* — Melanie Tyson
*Assistant Examiner* — Sidharth Kapoor
(74) *Attorney, Agent, or Firm* — Nathan S. Smith; McDermott Will & Emery LLP

(57) ABSTRACT

A device for delivering an expandable member to a luminal structure in a patient is described. In some embodiments, the device has a carrier member, with a carrier lumen extending at least partially therethrough. The device can have an elongate member that extends through the carrier lumen across a first notch in the carrier member. The device can have an expandable member that expands within and engages the luminal structure, can be carried by the carrier member, and has a first portion that fits within the first notch. When the elongate member extends through the carrier lumen and across the first notch, the elongate member secures the first portion to the carrier member. The elongate member is configured to move axially through the carrier lumen such that the elongate member permits release of the first portion from the carrier member and expansion of at least part of the expandable member.

34 Claims, 18 Drawing Sheets

(56) References Cited

U.S. PATENT DOCUMENTS

| | | |
|---|---|---|
| 4,013,063 A | 3/1977 | Bucalo |
| 4,245,623 A | 1/1981 | Erb |
| 4,553,545 A | 11/1985 | Maass et al. |
| 4,649,922 A | 3/1987 | Wiktor |
| 4,682,592 A | 7/1987 | Thorsgard |
| 4,705,517 A | 11/1987 | DiPisa, Jr. |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,370 A | 9/1992 | McNamara et al. |
| 5,234,437 A | 8/1993 | Sepetka |
| 5,242,451 A | 9/1993 | Harada et al. |
| 5,242,452 A | 9/1993 | Inoue |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A * | 12/1995 | Limon .................... 623/1.11 |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,607,445 A | 3/1997 | Summers |
| 5,656,036 A | 8/1997 | Palmaz |
| 5,674,287 A | 10/1997 | Slepian et al. |
| 5,693,083 A | 12/1997 | Baker et al. |
| 5,725,552 A | 3/1998 | Kotula et al. |
| 5,733,329 A | 3/1998 | Wallace et al. |
| 5,772,668 A * | 6/1998 | Summers et al. ............. 623/1.11 |
| 5,782,860 A | 7/1998 | Epstein et al. |
| 5,797,952 A * | 8/1998 | Klein .................... 623/1.12 |
| 5,797,953 A | 8/1998 | Tekulve |
| 5,830,222 A | 11/1998 | Makower |
| 5,846,261 A | 12/1998 | Kotula et al. |
| 5,868,782 A | 2/1999 | Frantzen |
| 5,902,266 A | 5/1999 | Leone et al. |
| 5,922,009 A | 7/1999 | Epstein et al. |
| 5,925,063 A | 7/1999 | Khosravi |
| 5,925,074 A | 7/1999 | Gingras et al. |
| 5,928,260 A | 7/1999 | Chin et al. |
| 5,944,738 A | 8/1999 | Amplatz et al. |
| 5,954,766 A | 9/1999 | Zadno-Azizi et al. |
| 5,957,929 A * | 9/1999 | Brenneman ................. 623/1.11 |
| 5,979,446 A | 11/1999 | Loy |
| 6,010,517 A | 1/2000 | Baccaro |
| 6,019,779 A * | 2/2000 | Thorud et al. ............... 606/198 |
| 6,024,765 A | 2/2000 | Wallace et al. |
| 6,056,770 A | 5/2000 | Epstein et al. |
| 6,059,825 A | 5/2000 | Hobbs et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,283,983 B1 | 9/2001 | Makower et al. |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,506,204 B2 | 1/2003 | Mazzocchi |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Epstein et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |
| 6,974,473 B2 | 12/2005 | Barclay et al. |
| 6,984,244 B2 | 1/2006 | Perez et al. |
| 7,001,409 B2 | 2/2006 | Amplatz |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |
| 7,398,780 B2 | 7/2008 | Callister et al. |
| 7,458,986 B2 | 12/2008 | Schmitt |
| 7,476,232 B2 | 1/2009 | Deal |
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,361 B2 | 8/2010 | Nikolchev et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,955,343 B2 | 6/2011 | Makower et al. |

(56) References Cited

U.S. PATENT DOCUMENTS

| | | |
|---|---|---|
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 * | 2/2012 | Melsheimer ............ 623/1.11 |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0153972 A1 | 8/2003 | Helmus |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0029994 A1 | 2/2004 | Cheng et al. |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0116714 A1 | 6/2006 | Sepetka et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0269719 A1 | 10/2008 | Balgobin |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 * | 5/2009 | Watson ............ 623/1.11 |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0106235 A1 | 4/2010 | Kariniemi et al. |
| 2010/0114307 A1 | 5/2010 | Agnew et al. |
| 2010/0121370 A1 | 5/2010 | Kariniemi |

(56) References Cited

U.S. PATENT DOCUMENTS

| | | |
|---|---|---|
| 2010/0174269 A1 | 7/2010 | Tompkins et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268201 A1 | 10/2010 | Tieu et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089216 A1 | 4/2012 | Rapaport et al. |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1 | 11/2012 | Kunis |
| 2012/0289988 A1 | 11/2012 | Riina et al. |
| 2012/0289994 A1 | 11/2012 | Larson et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0128780 A1 | 5/2014 | Kennedy et al. |
| 2014/0215792 A1 | 8/2014 | Leopold et al. |
| 2014/0222059 A1 | 8/2014 | Leopold et al. |

FOREIGN PATENT DOCUMENTS

| | | |
|---|---|---|
| EP | 1188413 | 3/2002 |
| EP | 1317908 A2 | 6/2003 |
| EP | 1600110 | 11/2005 |
| EP | 1707233 A2 | 10/2006 |
| EP | 1752112 | 2/2007 |
| EP | 1813196 | 8/2007 |
| EP | 1820436 A2 | 8/2007 |
| EP | 1852073 | 11/2007 |
| EP | 2248471 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 A | 2/2005 |
| GB | 2494820 A | 3/2013 |
| JP | H 07-000405 | 1/1995 |
| JP | 07-18501 | 7/1995 |
| JP | 2006-181015 A | 7/2006 |
| JP | 2010-532180 A | 10/2010 |
| JP | 2012-525859 A | 10/2012 |
| WO | WO-83/00997 | 3/1983 |
| WO | WO-92/14408 | 9/1992 |
| WO | WO-94/00179 A1 | 1/1994 |
| WO | WO-95/24158 | 9/1995 |
| WO | WO-95/25480 A1 | 9/1995 |
| WO | WO-95/32018 | 11/1995 |
| WO | WO-96/18361 | 6/1996 |
| WO | WO-97/13463 | 4/1997 |
| WO | WO-97/13471 | 4/1997 |
| WO | WO-97/27893 | 8/1997 |
| WO | WO-97/27897 | 8/1997 |
| WO | WO-97/27898 | 8/1997 |
| WO | WO-97/31672 | 9/1997 |
| WO | WO-98/08456 | 3/1998 |
| WO | WO-98/31308 | 7/1998 |
| WO | WO-98/34546 | 8/1998 |
| WO | WO-98/46115 A2 | 10/1998 |
| WO | WO-98/46119 | 10/1998 |
| WO | WO-99/12484 | 3/1999 |
| WO | WO-99/23976 | 5/1999 |
| WO | WO-99/25273 | 5/1999 |
| WO | WO-99/44542 A2 | 9/1999 |
| WO | WO-99/48545 | 9/1999 |
| WO | WO-99/49793 | 10/1999 |
| WO | WO-99/49910 A2 | 10/1999 |
| WO | WO-99/62430 | 12/1999 |
| WO | WO-00/09195 | 2/2000 |
| WO | WO-00/16847 | 3/2000 |
| WO | WO-00/27303 A2 | 5/2000 |
| WO | WO-00/67671 | 11/2000 |
| WO | WO-01/32254 | 5/2001 |
| WO | WO-01/64112 A1 | 9/2001 |
| WO | WO-01/80776 | 11/2001 |
| WO | WO-01/80777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 | 9/2003 |
| WO | WO-03/073962 | 9/2003 |
| WO | WO-03/101518 | 12/2003 |
| WO | WO-2004/006804 | 1/2004 |
| WO | WO-2004/073557 A2 | 9/2004 |
| WO | WO-2005/020786 A2 | 3/2005 |
| WO | WO-2005/092241 | 10/2005 |
| WO | WO 2005/117755 A2 | 12/2005 |
| WO | WO-2006/017470 A2 | 2/2006 |
| WO | WO-2006/028943 | 3/2006 |
| WO | WO-2006/031602 | 3/2006 |
| WO | WO-2006/034153 A2 | 3/2006 |
| WO | WO-2006/074163 A2 | 7/2006 |
| WO | WO-2006/096342 | 9/2006 |
| WO | WO-2006/111801 A2 | 10/2006 |
| WO | WO-2006/134354 | 12/2006 |
| WO | WO-2007/061927 A2 | 5/2007 |
| WO | WO-2007/070544 A2 | 6/2007 |
| WO | WO-2007/085373 | 8/2007 |
| WO | WO-2007/127351 | 11/2007 |
| WO | WO-2007/149844 A2 | 12/2007 |
| WO | WO-2008/010197 A2 | 1/2008 |
| WO | WO-2008/100790 A2 | 8/2008 |
| WO | WO-2008/112501 A2 | 9/2008 |
| WO | WO-2008/153653 | 12/2008 |
| WO | WO-2009/064618 | 5/2009 |
| WO | WO-2009/077845 A2 | 6/2009 |
| WO | WO-2009/088905 | 7/2009 |
| WO | WO-2009/124288 | 10/2009 |
| WO | WO-2009/126747 | 10/2009 |
| WO | WO-2010/009019 | 1/2010 |

(56) References Cited

FOREIGN PATENT DOCUMENTS

| WO | WO-2010/047644 | 4/2010 |
|---|---|---|
| WO | WO-2010/075565 A2 | 7/2010 |
| WO | WO-2010/085344 A1 | 7/2010 |
| WO | WO-2010/096717 | 8/2010 |
| WO | WO-2010/130617 | 11/2010 |
| WO | WO-2010/135352 A1 | 11/2010 |
| WO | WO-2010/146581 | 12/2010 |
| WO | WO-2010/148246 A2 | 12/2010 |
| WO | WO-2011/011581 A2 | 1/2011 |
| WO | WO-2011/153304 | 12/2011 |
| WO | WO-2011/163157 A2 | 12/2011 |
| WO | WO-2012/002944 | 1/2012 |
| WO | WO-2012/040380 | 3/2012 |
| WO | WO-2012/067724 | 5/2012 |
| WO | WO-2012/109367 | 8/2012 |
| WO | WO-2012/111137 | 8/2012 |
| WO | WO-2012/120490 A2 | 9/2012 |
| WO | WO-2012/131672 A2 | 10/2012 |
| WO | WO-2012/134761 | 10/2012 |
| WO | WO-2012/135859 A2 | 10/2012 |
| WO | WO-2012/166804 | 12/2012 |
| WO | WO-2013/055703 A1 | 4/2013 |
| WO | WO-2013/059511 A1 | 4/2013 |
| WO | WO-2013/067299 | 5/2013 |

OTHER PUBLICATIONS

Berguer et al., Cure by Combination of Operation and Detachable Intravascular Balloon, Ann. Surg. Jul. 1982, pp. 65-68, vol. 196, No. 1.

Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.

DeSouza et al., Embolization with Detachable Balloons—Applications Outside the Head, Clinical Radiology, Apr. 21, 1992, pp. 170-175, vol. 46.

Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.

Hawkins et al., The Permeability of Detachable Latex Rubber Balloons—An In Vitro Study, Investigative Radiology, Dec. 1987, pp. 969-972, vol. 22.

Hirai et al., Emergency Balloon Embolization for Carotid Artery Rupture Secondary to Postoperative Infection, Cardiovasc Intervent Radiol, 1996, pp. 50-52, vol. 19.

Kadir et al., Therapeutic Embolization of the Kidney with Detachable Silicone Balloons, The Journal of Urology, Jan. 1983, pp. 11-13, vol. 129.

Kallmes et al., The Use of Hydrocoil for Parent Artery Occlusion, AJNR Am J Neuroradiol, Sep. 2004, pp. 1409-1410, vol. 25.

Kaufman, et al., Detachable Balloon-Modified Reducing Stent to Treat Hepatic Insufficiency After Transjugular Intrahepatic Portosystemic Shunt Creation, J Vasc Interv Radiol., May 2003, pp. 635-638, vol. 14, No. 5.

Luo, Chao-Bao et al., Endovascular Treatment of the Carotid Artery Rupture with Massive Hemorrhage, J. Chin Med Assoc., Mar. 2003.

Makita, et al., Guide-Wire-directed Detachable Balloon: Clinical Application in Treatment of Varicoceles, Radiology, 1992, pp. 575-577, vol. 183.

Marshall et al., Treatment of Traumatic Renal Arteriovenous Fistulas by Detachable Silicone Balloon Embolization, The Journal of Urology, Aug. 1979, pp. 237-239, vol. 122.

Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.

Pollak et al., Clinical Results of Transvenous Systemic Embolotherapy with a Neuroradiologic Detachable Balloon, Radiology, May 1994, pp. 477-482, vol. 191, No. 2.

Reidy et al., Transcatherer Occlusion of Coronary to Bronchial Anastomosis by Detachable Balloon Combined with Coronary Angioplasty at Same Procedure, Brit Heart J. 1983, pp. 284-287, vol. 49.

Reidy et al., Transcatheter Occlusion of a Blalock-Taussig Shunt with a Detachable Balloon in a Child, Bri Heart Journal, 1983, pp. 101-103, vol. 50.

Ross et al., The Vascular Plug: A New Device for Parent Artery Occlusion, AJNR Am J Neuroradiol, Feb. 2007, pp. 385-386, vol. 28.

Serbinenko, F.A., Balloon Catheterization and Occlusion of Major Cerebral Vessels, J. Neurosurg. Aug. 1974, pp. 125-145, vol. 41.

Tasar, et al., Intrahepatic Arterioportal Fistula and its Treatment with Detachable Balloon and Transcatheter Embolization with Coils and Microspheres, Journal of Clinical Imaging, 2005, pp. 325-330, vol. 29.

Wehman, et al., Giant Cerebral Aneurysms: Endovascular Challenges, Neurosurgery, Nov. 2006, pp. S125-S138, vol. 59, No. 5.

White, et al., Occlusion of Varicoceles with Detachable Balloons, Radiology, May 1981, pp. 327-334, vol. 139.

Serbinenko, F.A., Occlusion by Balooning of Sacular Aneurysms of the Cerebral Arteries, Vopr, Neirokhir, Jul.-Aug. 1974, pp. 8-15, vol. 4.

Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.

U.S. Appl. No. 13/828,974, filed Mar. 14, 2013.
U.S. Appl. No. 14/044,794, filed Oct. 2, 2013.
U.S. Appl. No. 14/101,171, filed Dec. 9, 2013.
U.S. Appl. No. 14/281,797, filed May 19, 2014.

\* cited by examiner

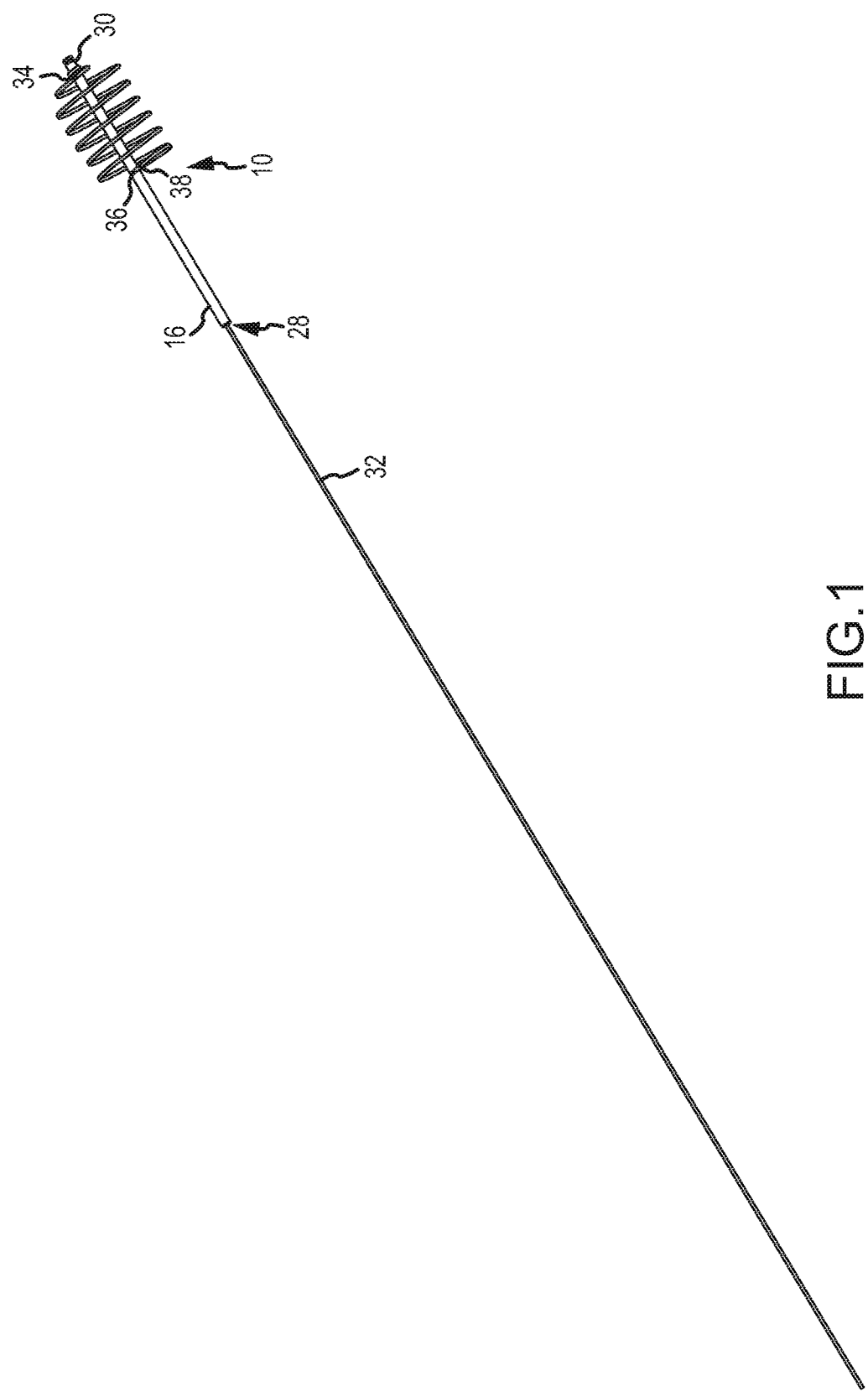

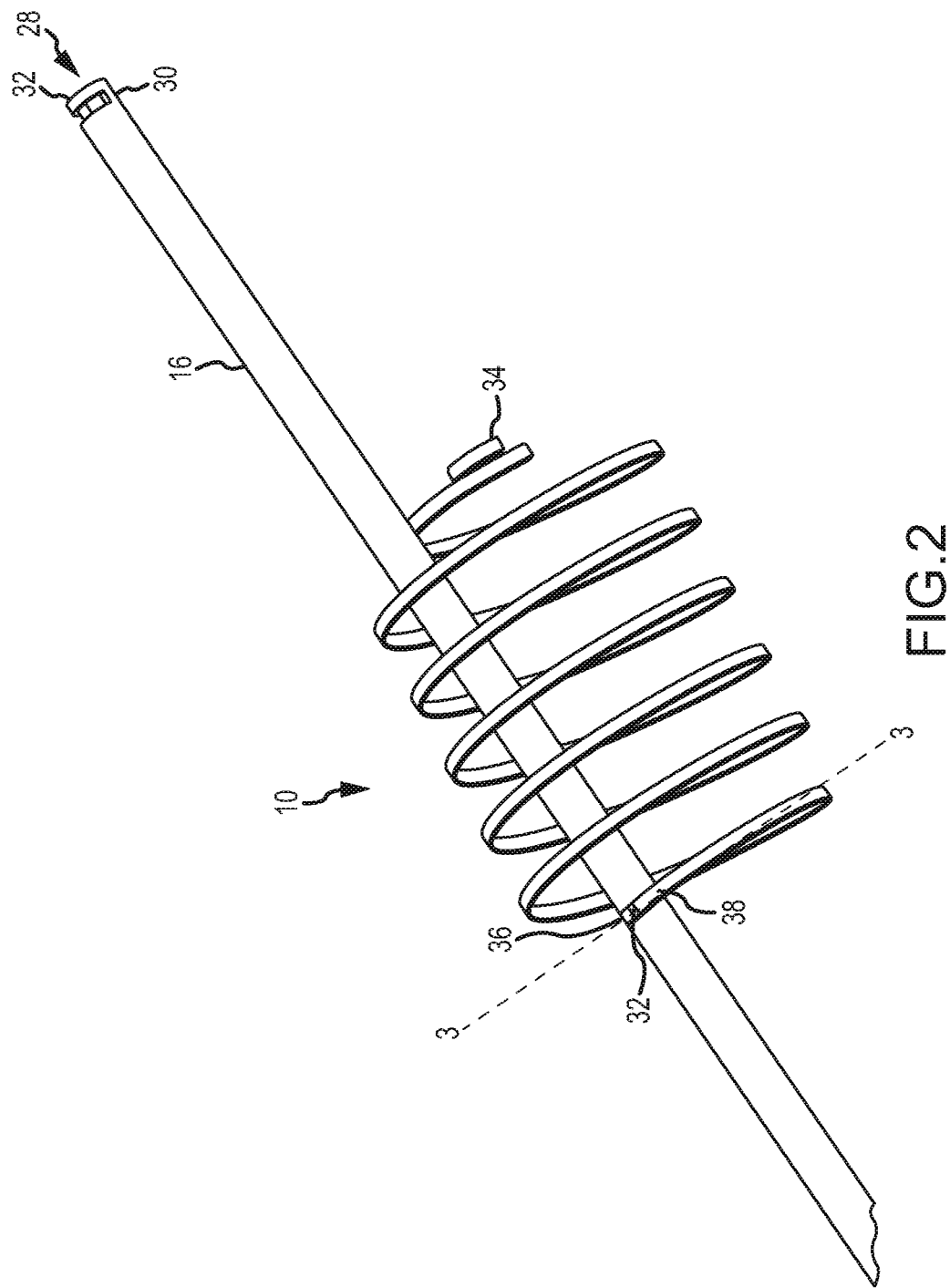

_EXPANDABLE DEVICE DELIVERY_

FIELD

The present invention generally relates to methods and devices for delivering an expandable member to a luminal structure in a patient.

BACKGROUND

Devices exist for stenting luminal structures in patients. Stents typically maintain patency in luminal structures such as blood vessels. As a result, flow of fluid such as blood through the luminal structures is generally maintained.

SUMMARY

Problems associated with typical devices for occluding flow through luminal structures of patients include inaccurate positioning and engagement of these devices within the luminal structures, as well as having continuous and significant residual flow. These devices, once placed, do not provide mechanisms allowing for their repositioning and/or removal in a simple manner. Thus, once these devices have been placed, the devices are typically committed to their initially placed positions. It is therefore desirable to provide devices that can be used to reduce or stop flow through a luminal structure in a patient, and also allow for their repositioning and/or removal.

According to various embodiments of the subject technology, a device is provided for delivering an expandable member to a luminal structure in a patient. The device comprises a carrier member, positionable in a luminal structure in a patient and having a cross-sectional area. The cross-sectional area comprises a first half and a second half that are separated by a line segment. The line segment intersects a point along a central long axis of the carrier member. The carrier member further has a carrier lumen extending axially at least partially through the carrier member and intersecting solely the first half of the cross-sectional area. The device also comprises a first notch in the carrier member, wherein, when the carrier member is positioned in the luminal structure, the carrier lumen is in fluid communication with a body fluid in the luminal structure at the first notch. The device comprises an elongate member that extends through the carrier lumen across the first notch, and an expandable member configured to expand within and engage the luminal structure and to be carried by the carrier member, and having a first portion that fits within the first notch. When the elongate member extends through the carrier lumen and across the first notch, the elongate member secures the first portion to the carrier member. When the first portion is secured to the carrier member, the first portion intersects solely the first half. The elongate member is configured to move axially through the carrier lumen such that the elongate member permits release of the first portion from the carrier member and expansion of at least part of the expandable member.

In some embodiments, the elongate member is configured to be retracted by an operator such that the elongate member permits the release of the first portion. In some embodiments, the elongate member permits the release of the first portion when the elongate member does not fully extend across the first notch. In some embodiments, the elongate member comprises a wire. In some embodiments, when expanded within and engaging the luminal structure, the expandable member substantially reduces flow of the body fluid through the luminal structure. In some embodiments, the expandable member fully obstructs flow of the body fluid through the luminal structure. In some embodiments, the expandable member is helically arranged about the carrier member. In some embodiments, the expandable member is coiled around the carrier member before being released from the carrier member.

In some embodiments, the device further comprises a catheter through which the carrier member moves when positioned within the luminal structure. In some embodiments, when the elongate member secures the first portion to the carrier member, the elongate member lies exterior to the first portion relative to the central long axis of the carrier member.

According to certain embodiments, the device further comprises a second notch in the carrier member. When the carrier member is positioned in the luminal structure, the carrier lumen is in fluid communication with a body fluid in the luminal structure at the second notch. The elongate member extends through the carrier lumen across the second notch. The expandable member comprises a second portion that fits within the second notch. When the elongate member extends through the carrier lumen and across the second notch, the elongate member secures the second portion to the carrier member. When the second portion is secured to the carrier member, the second portion intersects solely the first half. The elongate member is configured to move axially through the carrier lumen, after the first portion is released from the carrier member, such that the elongate member permits release of the second portion from the carrier member and release of the expandable member from the carrier member. In some embodiments, when the elongate member secures at least one of the first portion and the second portion to the carrier member, the elongate member lies exterior to at least one of the first portion and the second portion relative to the central long axis of the carrier member.

According to various embodiments of the subject technology, a method for delivering an expandable member to a luminal structure in a patient is provided. The method comprises positioning a carrier member in a luminal structure in a patient. The carrier member has a cross-sectional area comprising a first half and a second half that are separated by a line segment intersecting a point along a central long axis of the carrier member. The carrier member further has a carrier lumen extending at least partially through the carrier member and intersecting solely the first half. The carrier member has a first notch. When the carrier member is positioned in the luminal structure, the carrier lumen is in fluid communication with a body fluid in the luminal structure at the first notch. An elongate member extends through the carrier lumen across the first notch. An expandable member is carried by the carrier member and includes a first portion that fits within the first notch. The expandable member is configured to expand within and engage the luminal structure. When the elongate member extends through the carrier lumen and across the first notch, the elongate member secures the first portion to the carrier member. When the first portion is secured to the carrier member, the first portion intersects solely the first half. The method also comprises moving the elongate member axially through the carrier lumen such that the elongate member permits release of the first portion from the carrier member and expansion of at least part of the expandable member.

In some embodiments, the moving comprises retracting the elongate member by an operator who is performing the retracting. In some embodiments, the elongate member permits the release of the first portion when the elongate member does not fully extend across the first notch. In some embodiments, the expandable member is helically arranged about the carrier member. In some embodiments, the expandable member is coiled around the carrier member before being released from the carrier member. In some embodiments, when the elongate member secures the first portion to the carrier member, the elongate member lies exterior to the first portion relative to the central long axis of the carrier member. In some embodiments, the elongate member comprises a wire.

According to certain embodiments, the method further comprises moving the carrier member through a catheter when positioning the carrier member within the luminal structure.

According to certain embodiments, the method further comprises substantially reducing, with the expandable member, flow of the body fluid through the luminal structure when the expandable member is expanded within and engaging the luminal structure. In some embodiments, the method further comprises fully obstructing, with the expandable member, flow of the body fluid through the luminal structure when the expandable member is expanded within and engaging the luminal structure.

According to certain embodiments, the carrier member further comprises a second notch. When the carrier member is positioned in the luminal structure, the carrier lumen is in fluid communication with a body fluid in the luminal structure at the second notch. The elongate member extends through the carrier lumen across the second notch. The expandable member comprises a second portion that fits within the second notch. When the elongate member extends through the carrier lumen and across the second notch, the elongate member secures the second portion to the carrier member. When the second portion is secured to the carrier member, the second portion intersects solely the first half. The method further comprises moving, after the first portion is released from the carrier member, the elongate member axially through the carrier lumen such that the elongate member permits release of the second portion from the carrier member and release of the expandable member from the carrier member. In some embodiments, when the elongate member secures at least one of the first portion and the second portion to the carrier member, the elongate member lies exterior to at least one of the first portion and the second portion relative to the central long axis of the carrier member.

According to various embodiments of the subject technology, a device for delivering an expandable member to a luminal structure in a patient is provided. The device comprises a carrier member, positionable in a luminal structure in a patient and having a carrier lumen extending axially at least partially through the carrier member. The carrier lumen is bounded by a boundary having a boundary cross-sectional shape. The device also comprises a first notch in the carrier member, wherein, when the carrier member is positioned in the luminal structure, the carrier lumen is in fluid communication with a body fluid in the luminal structure at the first notch. The boundary has a first discontinuity at the first notch, between a first boundary end and a second boundary end. The device comprises an elongate member that extends through the carrier lumen and across the first notch. A first projection, having a cross-sectional shape that is substantially the same as the boundary cross-sectional shape, extends from the first boundary end, across the first discontinuity, to the second boundary end. The device comprises an expandable member configured to expand within and engage the luminal structure and to be carried by the carrier member, and having a first portion comprising a first free end. The first portion fits within the first notch. In some embodiments, when the elongate member extends through the carrier lumen and across the first notch, and when the elongate member secures the first portion to the carrier member, the first free end lies outside the first projection and/or the boundary. In some embodiments, the elongate member is configured to move axially through the carrier lumen such that the elongate member permits release of the first portion from the carrier member and expansion of at least part of the expandable member.

In some embodiments, the carrier member has a cross-sectional area comprising a first half and a second half that are separated by a line segment intersecting a point along a long axis of the carrier member. In some embodiments, the carrier lumen intersects solely the first half. In some embodiments, when the first portion is secured to the carrier member, the first portion intersects solely the first half.

According to certain embodiments, the device further comprises a second notch in the carrier member. When the carrier member is positioned in the luminal structure, the carrier lumen is in fluid communication with a body fluid in the luminal structure at the second notch. The boundary has a second discontinuity at the second notch, between a third boundary end and a fourth boundary end. The elongate member extends through the carrier lumen and across the second notch. A second projection, having a cross-sectional shape that is substantially the same as the boundary cross-sectional shape, extends from the third boundary end, across the second discontinuity, to the fourth boundary end. The expandable member comprises a second portion comprising a second free end, the second portion fitting within the second notch. In some embodiments, when the elongate member extends through the carrier lumen and across the second notch, and when the elongate member secures the second portion to the carrier member, the second free end lies outside the second projection and/or the boundary. In some embodiments, the elongate member is configured to move axially through the carrier lumen, after the first portion is released from the carrier member, such that the elongate member permits release of the second portion from the carrier member and release of the expandable member from the carrier member.

In some embodiments, when the second portion is secured to the carrier member, the second portion intersects solely the first half. In some embodiments, when the elongate member secures at least one of the first portion and the second portion to the carrier member, the elongate member lies exterior to at least one of the first portion and the second portion relative to the central long axis of the carrier member. In some embodiments, the first projection is collinear with the boundary.

According to certain embodiments, the elongate member is configured to be retracted by an operator such that the elongate member permits the release of the first portion. The elongate member permits the release of the first portion when the elongate member does not fully extend across the first notch. In some embodiments, the elongate member comprises a wire. When expanded within and engaging the luminal structure, the expandable member substantially reduces flow of the body fluid through the luminal structure. In some embodiments, the expandable member fully obstructs flow of the body fluid through the luminal structure.

According to certain embodiments, the expandable member is helically arranged about the carrier member. The expandable member is coiled around the carrier member before being released from the carrier member. In some embodiments, the device further comprises a catheter through which the carrier member moves when being positioned within the luminal structure. In some embodiments, when the elongate member secures the first portion to the carrier member, the elongate member lies exterior to the first portion relative to a central long axis of the carrier member.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

FIG. 1 illustrates an example of a device for reducing or stopping flow through a luminal structure in a patient, in accordance with various embodiments of the subject technology.

FIG. 2 illustrates a detailed view of the example of FIG. 1, in accordance with various embodiments of the subject technology.

DETAILED DESCRIPTION

Figure 3A:
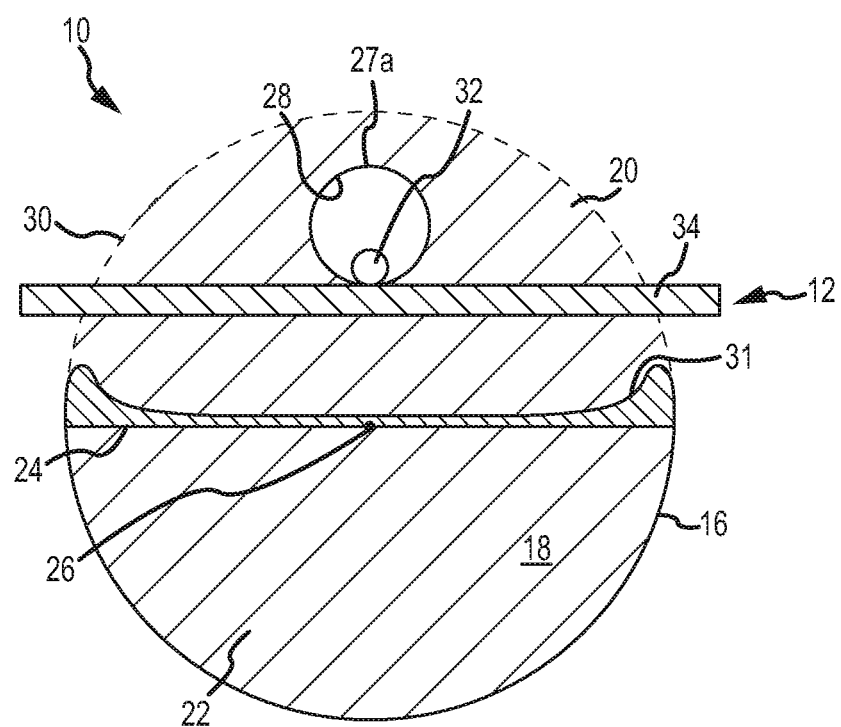
FIG. 3A illustrates a cross sectional view of the example of FIGS. 1 and 2, taken along line 3-3 of FIG. 2, and having a first portion of an expandable member fitting in a first notch of a carrier member and an elongate member extending across the first notch, in accordance with various embodiments of the subject technology.
Figure 3B:
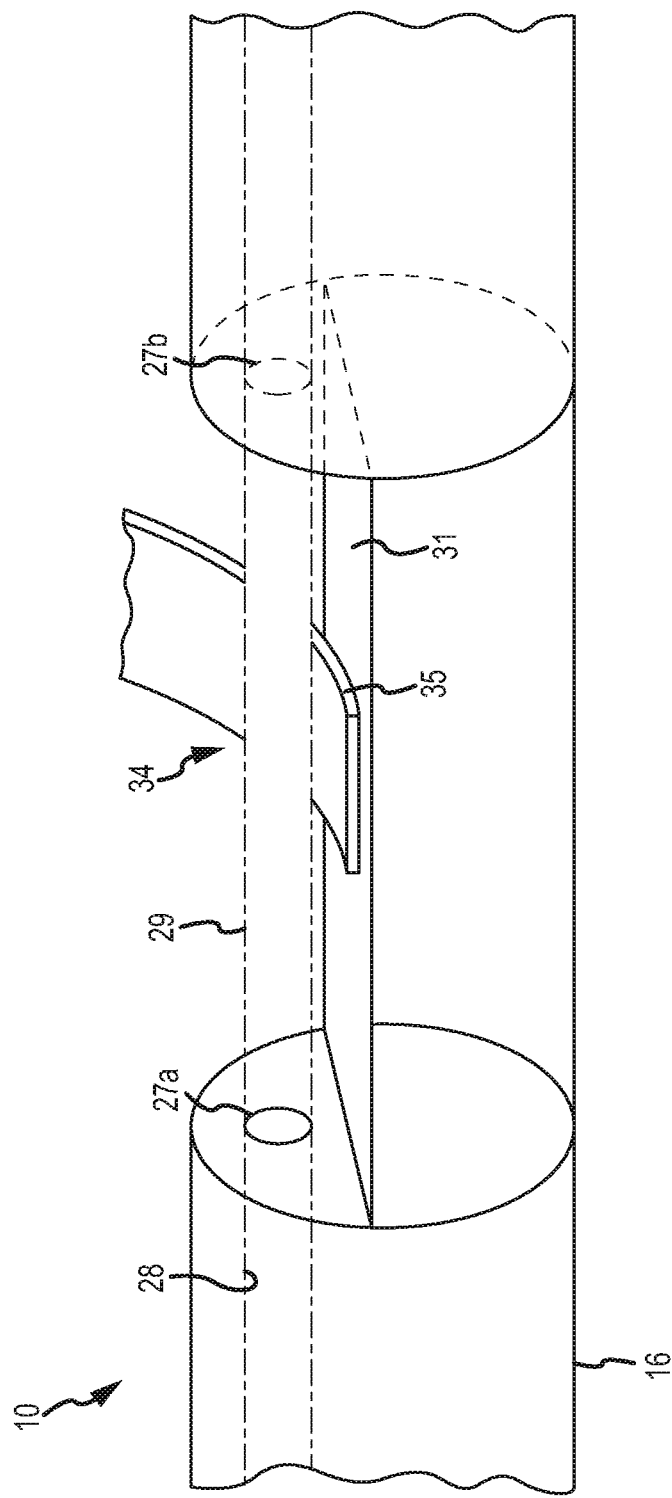
FIG. 3B illustrates a perspective view of an example of a first portion of an expandable member fitting in a first notch of a carrier member, in accordance with various embodiments of the subject technology.
Figure 4:
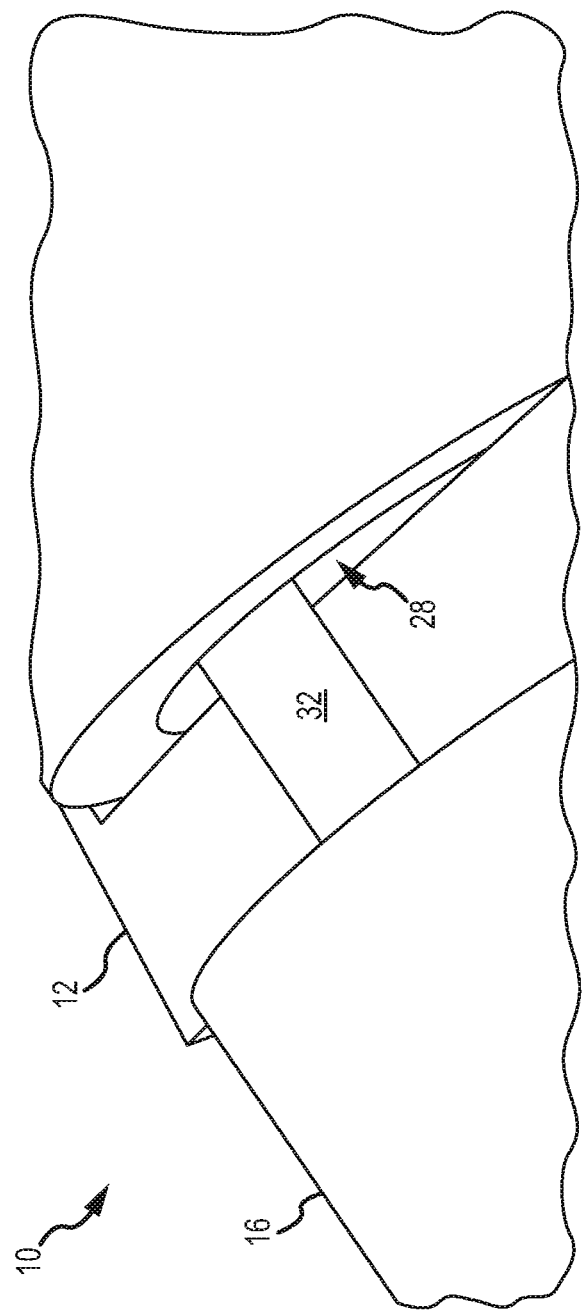
FIG. 4 illustrates a detailed view of the example of FIGS. 1-3A, showing the first portion of the expandable member in the first notch, in accordance with various embodiments of the subject technology.

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

FIGS. 1-4 illustrate an example of device 10 for delivering expandable member 12 to luminal structure 14 (illustrated in FIGS. 9-12) in a patient to reduce or stop flow through luminal structure 14, in accordance with various embodiments of the subject technology. Device 10 comprises carrier member 16, positionable in luminal structure 14 in the patient. Referring to FIGS. 3A and 3B, carrier member 16 has cross-sectional area 18 comprising first half 20 and second half 22 that are separated by line segment 24 intersecting point 26 along a central long axis of carrier member 16. In some embodiments, carrier member 16 has carrier lumen 28 extending at least partially through carrier member 16 and intersecting solely first half 20. Carrier member 16 has first notch 30, wherein, when carrier member 16 is positioned in luminal structure 14, carrier lumen 28 is in fluid communication with a body fluid in luminal structure 14 at first notch 30. First notch 30 may be a notch or ring placed distally at a tip (e.g., about 1-2 mm from the end) of a distal edge of carrier member 16. Carrier member 16 may be nylon, stainless steel hypotube, or any other suitable material. According to certain embodiments, a proximal end of carrier member 16 is made of nylon with changeable durometer or stainless steel (optionally slotted for flexibility) hypotube, and a distal end of carrier member 16 is made of stainless steel hypotube, about 0.20-0.40" OD (0.5-1 mm). In some embodiments, carrier member 16 may have a solid cross-sectional area except where carrier lumen 28 extends and/or except where a notch (e.g., first notch 30) is formed on carrier member 16. For example, wall 31 of carrier member 16 may form an inner wall of first notch 30, and may be have a solid cross-sectional area covering at least second half 22. In some embodiments, wall 31 may have a smaller solid cross-sectional area provided that wall 31 forms the inner wall of first notch 30 (e.g., like a table separating a table top area from a table bottom area).

Device 10 also comprises elongate member 32 that extends through carrier lumen 28 across first notch 30 and expandable member 12 configured to expand within and engage luminal structure 14. Expandable member 12 is configured to be carried by carrier member 16 and has first portion 34 that fits within first notch 30. Elongate member 32 extends through carrier lumen 28 and across first notch 30, securing first portion 34 of expandable member 12 to carrier member 16. Elongate member 32 lies exterior to first portion 34, relative to the central long axis of carrier member 16 and may be micro welded in place. Elongate member 32 is configured to be retracted by an operator, permitting the release of first portion 34. When elongate member 32 does not fully extend across first notch 30, elongate member 32 permits the release of first portion 34. Elongate member 32 is illustrated as a tungsten wire. However, other elongated structures, such as ribbon, cable, small diameter hypotube, or other elongated materials may be used. In some embodiments, a cross-sectional diameter of carrier member 16 may be between 0.018 inches and 0.068 inches. In some embodiments, a combined cross-sectional diameter of carrier member 16 and elongate member 32 when elongate member 32 is carried by carrier member 16 may be between 0.018 inches and 0.068 inches.

In some embodiments, carrier lumen 28 is bounded by boundary 27 having a boundary cross-sectional shape, in accordance with various embodiments of the subject technology. The boundary cross-sectional shape may be at least one of an elliptical, rectangular, and polygonal shape. Boundary 27 has a first discontinuity at first notch 30, between first boundary end 27a and second boundary end 27b. In some embodiments, first projection 29, having a cross-sectional shape that is substantially the same as the boundary cross-sectional shape, extends from first boundary end 27a, across the first discontinuity, to second boundary end 27b. In some embodiments, elongate member 32 extends through first projection 29. In some embodiments, elongate member 32 has a cross-sectional shape that is substantially the same as the boundary cross-sectional shape. In some embodiments, elongate member 32 has a cross-sectional area that is less than a cross-sectional area of the boundary cross-sectional shape. In some embodiments, first projection 29 is collinear with boundary 27. First portion 34 comprises free end 35. In some embodiments, when elongate member 32 extends through carrier lumen 28 and across first notch 30, and when elongate member 32 secures first portion 34 to carrier member 16, first free end 35 lies outside first projection 29 and/or boundary 27. In some embodiments, "projection," as used herein, refers to a shape defining boundaries that has no physical manifestation. For example, first projection 29 may be a virtual cylinder and is not an actual physical structure. In some embodiments, "projection," as used herein, is given its plain ordinary meaning.

According to certain embodiments, carrier member 16 may further comprise second notch 36 wherein, when carrier member 16 is positioned in luminal structure 14, carrier lumen 28 is in fluid communication with a body fluid in luminal structure 14 at second notch 36. Elongate member 32 may extend through carrier lumen 28 across second notch 36 and expandable member 12 may have second portion 38 that fits within second notch 36. Elongate member 32 extends through carrier lumen 28 and across second notch 36, securing second portion 38 of expandable member 12 to carrier member 16. Elongate member 32 lies exterior to second portion 38, relative to the central long axis of carrier member 16 and may be micro welded in place. When second portion 38 of expandable member 12 is secured to carrier member 16, second portion 38 intersects solely first half 20. Elongate member 32 is configured to move axially through carrier lumen 28 after first portion 34 of expandable member 12 is released from carrier member 16, such that elongate member 32 permits release of second portion 38 from carrier member 16. Such release may be a final or complete release of expandable member 12 from carrier member 16. As illustrated in FIG. 1, a single elongate member 32 secures first portion 34 and second portion 38 of expandable member 12 to carrier member 16 at respective first notch 30 and second notch 36. Alternatively, separate elongate members may be used for each instance where a notch is provided in carrier member 16 for engagement with expandable member 12. For example, a first elongate member may be used with first notch 30 to secure first portion 34 of expandable member 12 to carrier member 16, while a second elongate member is used with second notch 36 to secure second portion 38 of expandable member to carrier member 16. In such an embodiment, the first and second elongate members may act completely independently, such that the first elongate member releases the first portion 34 and the second releases the second portion 38. Such a configuration may allow complete independence of distal release from proximal and vice versa. In some such embodiments, the first elongate member may be of uniform cross-section, while the second elongate member may be tapered from proximal to distal, and may serve as an internal kink-resistant support.

Device 10 may also comprise occlusion membrane 40 or other flow reducing member coupled to expandable member 12 such that when expandable member 12 is expanded within and engaging luminal structure 14, expandable member 12 substantially reduces flow of body fluid through luminal structure 14. When expandable member 12 is positioned within the lumen, occlusion membrane 40 may substantially reduce or fully obstruct flow of at least one of emboli and fluid flowing through the lumen. Occlusion membrane 40 may be secured and placed inside and/or outside of expandable member 12. In some aspects, occlusion membrane 40 may be coupled to expandable member 12 using surgical suture.

In some embodiments, expandable member 12 is arranged in a spiral or other helical configuration about carrier member 16. Expandable member 12 may be beneficially expanded in a radial direction to engage an inner surface of the lumen. Should the inner surface of the lumen apply a radially compressive force on any portion of expandable member 12, the spiral configuration of expandable member 12 allows for such a force to be dispersed along the entirety of expandable member 12, thereby providing strong structural support for expandable member 12 to be placed within the lumen. In some embodiments, the spiral configuration allows for expandable member 12 to withstand long-term pulsatile loads of torque and bending, and beneficially reduces risks of fatigue breaks, cracks, etc. In some embodiments, expandable member 12 may be arranged to have more or less coils in the spiral configuration depending on a desired size a desired placement, and a desired compressibility of expandable member 12, and other suitable factors known to those of ordinary skill in the art. In some embodiments, expandable member 12 is highly flexible while providing sufficient rigidity to be guided through the lumen. In some embodiments, tapered distal portion 42 comprises one to two coils of expandable member 12.

Although expandable member 12 is arranged in the spiral configuration, other suitable configurations known to those of ordinary skill in the art may be used. In some embodiments, expandable member 12 comprises one or more anchors configured to engage an inner surface of the lumen for resisting axial movement of expandable member 12 when expandable member 12 is deployed within the lumen. For example, the one or more anchors may be protrusions, or hair-like wires of the same material as expandable member 12.

According to certain embodiments, device 10 may be removed from within the lumen by inverting expandable member 12. For example, an axial force in the proximal direction may be applied to distal portion 42 such that distal portion 42 moves within and toward second portion 38. In some embodiments, such an inversion causes expandable member 12 to "unwind" from its spiral configuration, in which case the axial force may continue to be applied until expandable member 12 disengages from the inner surface of the lumen. In some embodiments, expandable member 12 may maintain its spiral configuration after the inversion, but otherwise have a reduced cross sectional dimension as an inverted expandable member 12. In such a case, the inverted expandable member 12 may be easily removed from within the lumen because of the reduced cross sectional dimension.

According to various embodiments of the subject technology, expandable member 12 may comprise at least one of stainless steel, nickel titanium (NiTi), cobalt chromium (CoCr), titanium, a polymer, a polyester based material, a tyrosine based polycarbonate, a polyethylene based material, Teflon (e.g., including expanded Teflon), and other suitable materials known to those of ordinary skill in the art. In some embodiments, expandable member 12 may comprise at least one of polyethylene, polyglicolide, polylactide, ϵ-caprolactone, polycarbonate, hydroxyalkanote, para dioxinine, polytetrafluoroethylene (PTFE), expanded polytetrafluoroethylene (ePTFE), PLA, PGA, PLLA, PDLLA, PDO, PCL, and other suitable materials known to those of ordinary skill in the art. In some embodiments, expandable member 12 and/or occlusion membrane 40, may comprise a bioabsorbable material, beneficially allowing for their controlled degradation. In some embodiments, expandable member 12 and/or occlusion membrane 40 may be formed of bioabsorbable material to have a controlled degradation anywhere between about 3 months to about 3 years depending on the desired application of device 10. In some embodiments, the controlled degradation may be less than about 3 months or greater than about 3 years. For example, hydrolysis of ester linkages or effects of enzymatic degradation may be utilized for the controlled degradation.

In some embodiments, expandable member 12 may be coated with various suitable agents to allow expandable member 12 to expand within and engage the inner surface of the lumen. For example, expandable member 12 may be coated with biological glue. In some embodiments, the biological glue may comprise glue from at least one of crab shells, spider webs, gecko feet, burrowing frogs, mussels, and caulobacter crescentus bacteria. In some embodiments, expandable member 12 may be coated with a friction-resistant coating (e.g., a friction-resistant polymer coating). In some embodiments, radio-opaque markers may be located on carrier member 16, expandable member 12, occlusion membrane 40, elongate member 32 and/or catheter 44 for endovascular or other image-guided procedures. For example, a radio-opaque marker may be placed on a first coil of expandable member 12. In some embodiments, an outer cross sectional dimension of the first coil is less than an outer cross sectional dimension of a second coil of expandable member 12, which will allow space for the radio-opaque marker to surround, at least in part, an exterior of the first coil. In some embodiments, the first coil is adjacent to the second coil, and occlusion membrane 40 may be coupled to the second coil. In this regard, having the radio-opaque marker placed on the first coil adjacent to the second coil that is coupled to occlusion membrane 40 will allow an operator of device 10 to identify where embolization may occur, for example. In some embodiments, the radio-opaque marker may be a platinum iridium alloy or other suitable markers known to those of ordinary skill in the art.

According to various embodiments of the subject technology, occlusion membrane 40 may be used to occlude, partially or completely, luminal structure 14 in which device 10 is deployed. In some embodiments as used herein, occlusion may refer to either partial or complete occlusion. In some embodiments, occlusion membrane 40 comprises at least one of a polyurethane, a polyanhidrate, PTFE, ePTFE, and other suitable materials known to those of ordinary skill in the art. In some embodiments, occlusion membrane 40 may be elastic. In some embodiments, occlusion membrane 40 may be permeable or non-permeable.

According to certain embodiments, occlusion membrane 40 forms a continuous cover without a flap. For example, occlusion membrane 40 may form a cover at distal portion 42. In some embodiments, occlusion membrane 40 may comprise a plurality of pores each having a diameter of between about 5 microns and about 10 microns, which may be beneficial for occluding blood, for example. In some embodiments, occlusion membrane 40 may comprise a plurality of pores each having a diameter less than about 5 microns or greater than about 10 microns. In some embodiments, occlusion membrane 40 may comprise a plurality of pores each having a diameter less than about 3 microns. In some embodiments, occlusion membrane 40 may comprise a plurality of pores each having a diameter less than about 1 micron. In some embodiments, occlusion membrane 40 may comprise a plurality of pores each having a diameter greater than about 13 microns. In some embodiments, occlusion membrane 40 may comprise a plurality of pores each having a diameter greater than about 16 microns. Although occlusion membrane 40 is shown as disposed at distal portion 42, occlusion membrane 40 may be disposed over other portions of expandable member 12 depending on the desired placement of occlusion membrane 40, desired application of device 10, etc. For example, occlusion membrane 40 may be disposed over a proximal portion or middle portion of expandable member 12. In another example, occlusion membrane 40 may be disposed over the proximal portion, middle portion, and distal portion 42.

In some embodiments, a length of expandable member 12 may be between about 7 millimeters (mm) and about 9 mm. In some embodiments, the length of expandable member 12 may be less than about 7 mm or greater than about 9 mm. According to certain embodiments, a combined length of the proximal portion and the middle portion may be between about 4 mm and about 5 mm to provide adequate anchoring of expandable member 12 with respect to distal portion 42 (e.g., between about 40% and about 70% of the length of expandable member 12). In some embodiments, the combined length of the proximal portion and the middle portion may be less than about 4 mm or greater than about 5 mm. In some embodiments, a length of distal portion 42 may be between about 3 mm and about 4 mm. In some embodiments, the length of distal portion may be less than about 3 mm or greater than about 4 mm. In some embodiments, a diameter of the proximal portion and/or the middle portion may be between about 2 mm and about 10 mm. In some embodiments, the diameter of the proximal portion and/or the middle portion may be less than about 2 mm or greater than about 10 mm. In some embodiments, a diameter of distal portion 42 may be between about 0.4 mm and about 0.5 mm. In some embodiments, the diameter of distal portion 42 may be less than about 0.4 mm or greater than about 0.5 mm.

In some embodiments, an average thickness of occlusion membrane 40 is between about 0.0005 inches and about 0.006 inches. In some aspects, the average thickness of occlusion membrane 40 may be less than about 0.0005 inches or greater than about 0.006 inches. In certain embodiments, an average thickness of a distal portion of occlusion membrane 40 is greater than an average thickness of a proximal portion of occlusion membrane 40. Such a configuration may ensure that more flow may be reduced at the distal portion of occlusion membrane 40. In some embodiments, the average thickness of the distal portion of occlusion membrane 40 is between about 0.002 inches and about 0.012 inches. In some embodiments, the average thickness of the distal portion of occlusion membrane 40 may be less than about 0.002 inches or greater than about 0.012 inches. In some embodiments, the average thickness of the proximal portion of occlusion membrane 40 is between about 0.0005 inches and about 0.006 inches. In some embodiments, the average thickness of the proximal portion of occlusion membrane 40 may be less than about 0.0005 inches or greater than about 0.006 inches.

According to various aspects of the subject technology, device 10 may be used for various applications for reducing or stopping flow through a luminal structure in a patient. Device 10 may be used for rapid, well-controlled, and reliable occlusion of luminal structures. For example, the luminal structure may comprise at least one of a blood vessel, a body organ, a lung, an airway, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. In some embodiments, device 10 may be used for temporary occlusion in cases of lung disease, or for temporary occlusion of female reproductive organs for contraceptive purposes. In some embodiments, device 10 may be removed, or flow may be restored through the luminal structure to restore original organ functions.

In some embodiments, device 10 may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). In some embodiments, device 10 may be used for stopping blood loss from a damaged blood vessel, closing an abnormal blood vessel or a blood vessel supplying a vascular anamaly, or interrupting blood supply to an organ or part of an organ for permanent devascularization (e.g., closure of splenic artery in spleen laceration, devascularization of tissues involved by neoplastic process, either pre-operatively or as a palliative measure). In some embodiments, device 10 may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, etc.), and devascularization prior to (or as an alternative to) surgical resection of various organs or tumors.

In certain embodiments, device 10 may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of uretero-arterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). The application of device 10 is not limited to applications for human patients, but may also include veterinary applications.

In some embodiments, device 10 comprises a tube configured to extend around or through occlusion membrane 40 to be positioned at a target site of the patient. Device 10 also comprises a vacuum source configured to apply a vacuum through the tube for removing at least one of emboli and fluid from the target site. For example, the tube may be placed in a diseased area that has been subjected to occlusion, and the tube may be used to remove body fluids and/or solid components (e.g., blood clots) from the diseased area.

Figure 5:
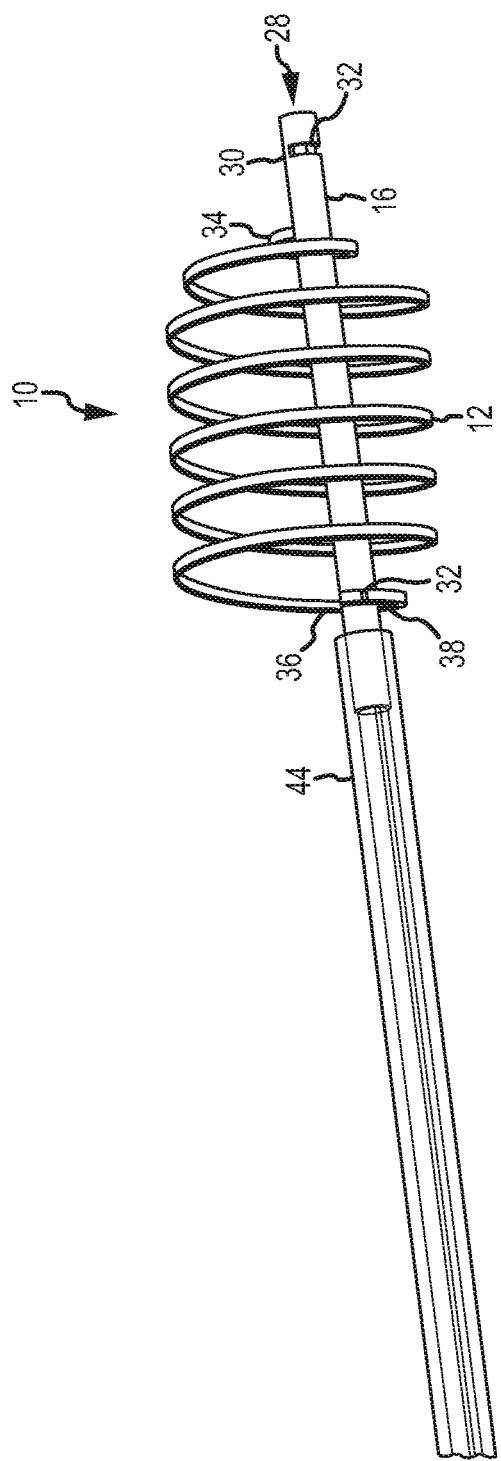
FIG. 5 illustrates an example of a device for reducing or stopping flow through a luminal structure in a patient, having a catheter and a first portion of an expandable member fitting in a first notch of a carrier member and an elongate member extending across the first notch, in accordance with various embodiments of the subject technology.

FIG. 5 illustrates an example of expandable member 12 in the process of being loaded on carrier member 16, in accordance with various embodiments of the subject technology. As illustrated, second portion 38 of expandable member 12 is fitted within second notch 36 and secured in place by elongate member 32. As first portion 34 of expandable member 12 is moved toward first notch 30 to be secured in place by elongate member 32, expandable member 12 will extend longitudinally while contracting radially. In addition to longitudinal extension, expandable member 12 may also be rotated about carrier member 16 such that expandable member 12 is compact enough to fit within catheter 44. Once first portion 34 of expandable member 12 is secured in first notch 30, carrier member 16 may be retracted relative to catheter 44. Carrier member 16, along with expandable member 12 may move through catheter 44 when being positioned within luminal structure 14.

In some aspects, "catheter" as used herein may be given at least its ordinary meaning. In some aspects, "catheter" as used herein may refer to any elongate member having a lumen passing therethrough. A catheter, therefore, can be tubular or have other suitable cross sectional shapes, such as at least one of elliptical and polygonal (e.g., triangular, rectangular, hexagonal, octagonal, etc.) cross sectional shapes. Catheter profile can be 4-7 french (or 1.3 to 2.3 mm), or in a range of 0.20" to 0.40". The length of catheter 44 can be 130-150 cm.

Figure 6:
FIG. 6 illustrates a catheter with a core and guide wire in a luminal structure of a patient, in accordance with various embodiments of the subject technology.

FIG. 6 illustrates an example of catheter 44 in the process of being positioned within luminal structure 14 at a deployment site, in accordance with various embodiments of the subject technology. Catheter 44 is introduced into the patient (e.g., via femoral artery) and navigated through luminal structure 14 and positioned at the deployment site. In some embodiments, guide wire 46 is inserted into luminal structure 14 and has a soft tip useful for reducing trauma and/or friction. Once guide wire 46 is in place, a guide catheter and/or core 48 is introduced, using guide wire 46 as a guide. Core 48 may be telescopically inserted, acting as an independent component, possessing a tapered soft distal tip (about 4-5 mm long) for better trackability of catheter 44 through the vascular or any other tortuous tubular system. Core 48 may then be used as a guide for the introduction of catheter 44 into luminal structure 14 and for the positioning of catheter 44 at the deployment site. Thus, a portion of catheter 44 is disposed over a portion of core 48, which is disposed over a portion of guide wire 46. After the position of catheter 44 is evaluated and confirmed at the target site (e.g., via flouro imaging), core 48 and guide wire 46 can be removed. Guide wire 46 may be absent when carrier member 16 and expandable member 12 with occlusion membrane 40 are introduced. Thus, occlusion membrane 40 may lack a hole for guide wire 46, allowing for enhanced occlusion. In some embodiments, delivery of expandable member 12 does not require guide wire 46 to run through occlusion membrane 40, thereby obviating the need to poke a hole through occlusion membrane 40 with guide wire 46 for delivery of expandable member 12.

Figure 7:
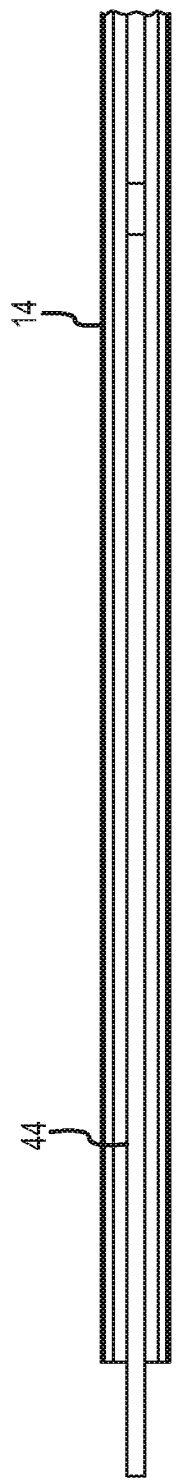
FIG. 7 illustrates the catheter of FIG. 6, with the core and guide wire removed, in accordance with various embodiments of the subject technology.

FIG. 7 illustrates an example of a catheter 44 positioned within luminal structure 14 at a deployment site, in accordance with various embodiments of the subject technology. Catheter 44 positioned within luminal structure 14 has an opening therethrough, through which device 10 may be introduced, and through which a portion of device 10 may at least partially emerge from a distal end. In some embodiments, catheter 44 may prevent expandable member 12 from radially expanding such that expandable member 12 is secured between the inner surface of catheter 44 and the outer surface of carrier member 16. In some embodiments, when carrier member 16 is shifted distally relative to catheter 44 until expandable member 12 extends beyond a distal opening of catheter 44 into the deployment site, catheter 44 no longer prevents expandable member 12 from radially expanding. In this regard, expandable member 12 may expand from an undeployed configuration into a partially deployed configuration such that expandable member 12 partially engages an inner surface of the lumen. In some embodiments, expandable member 12 does not automatically expand into a deployed configuration, but is expanded into the deployed configuration via actuation of elongate member 32. In some embodiments, expandable member 12 may be self expandable.

Figure 8:
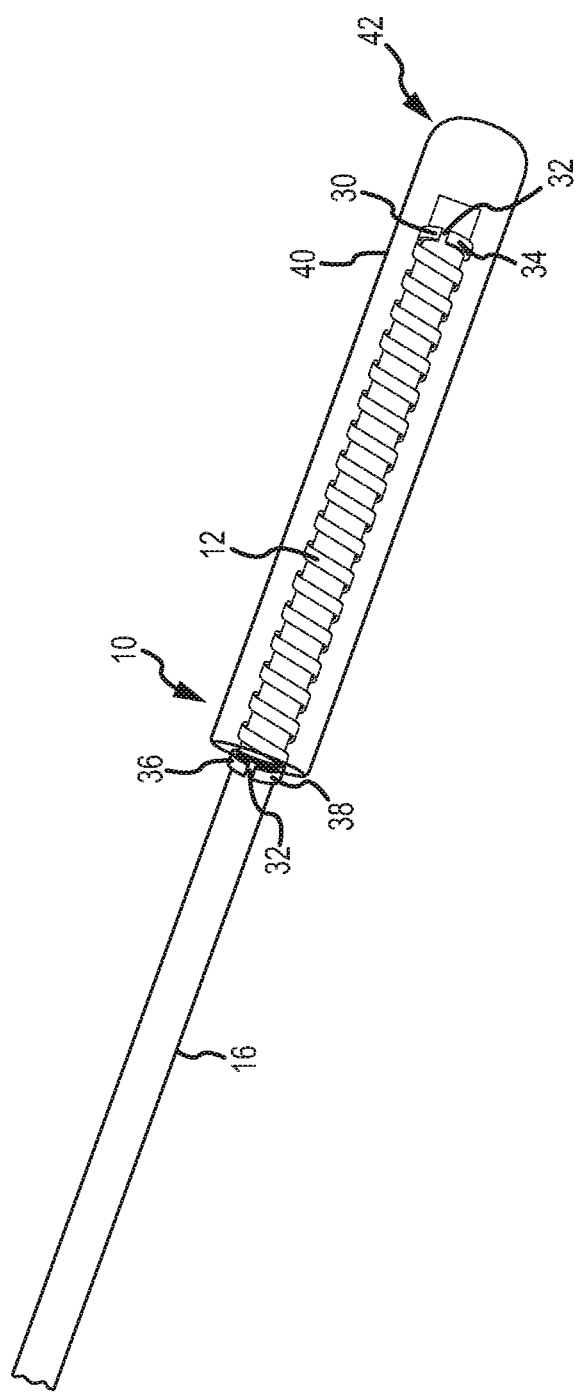
FIG. 8 illustrates an example of a device for reducing or stopping flow through a luminal structure in a patient, having a carrier member, with an expandable member fitting in a first notch and a second notch of the carrier member, and having an occlusion membrane positioned thereabout, in accordance with various embodiments of the subject technology.

FIG. 8 illustrates an example of device 10 in a position for placement in catheter 44, in accordance with various embodiments of the subject technology. Device 10 comprises carrier member 16, expandable member 12 with first portion 34 secured in first notch 30 via elongate member 32, and second portion 38 secured in second notch 36 via elongate member 32. Device 10 also comprises occlusion membrane 40 coupled to an exterior of expandable member 12. Expandable member 12 is configured to be positioned between carrier member 16 and catheter 44 for stowage of expandable member 12 before expandable member 12 is deployed within luminal structure 14. Distal portion 42 of expandable member 12 is loaded into catheter 44 and device 10 is positioned at or near the deployment site by moving carrier member 16 relative to catheter 44.

Figure 9:
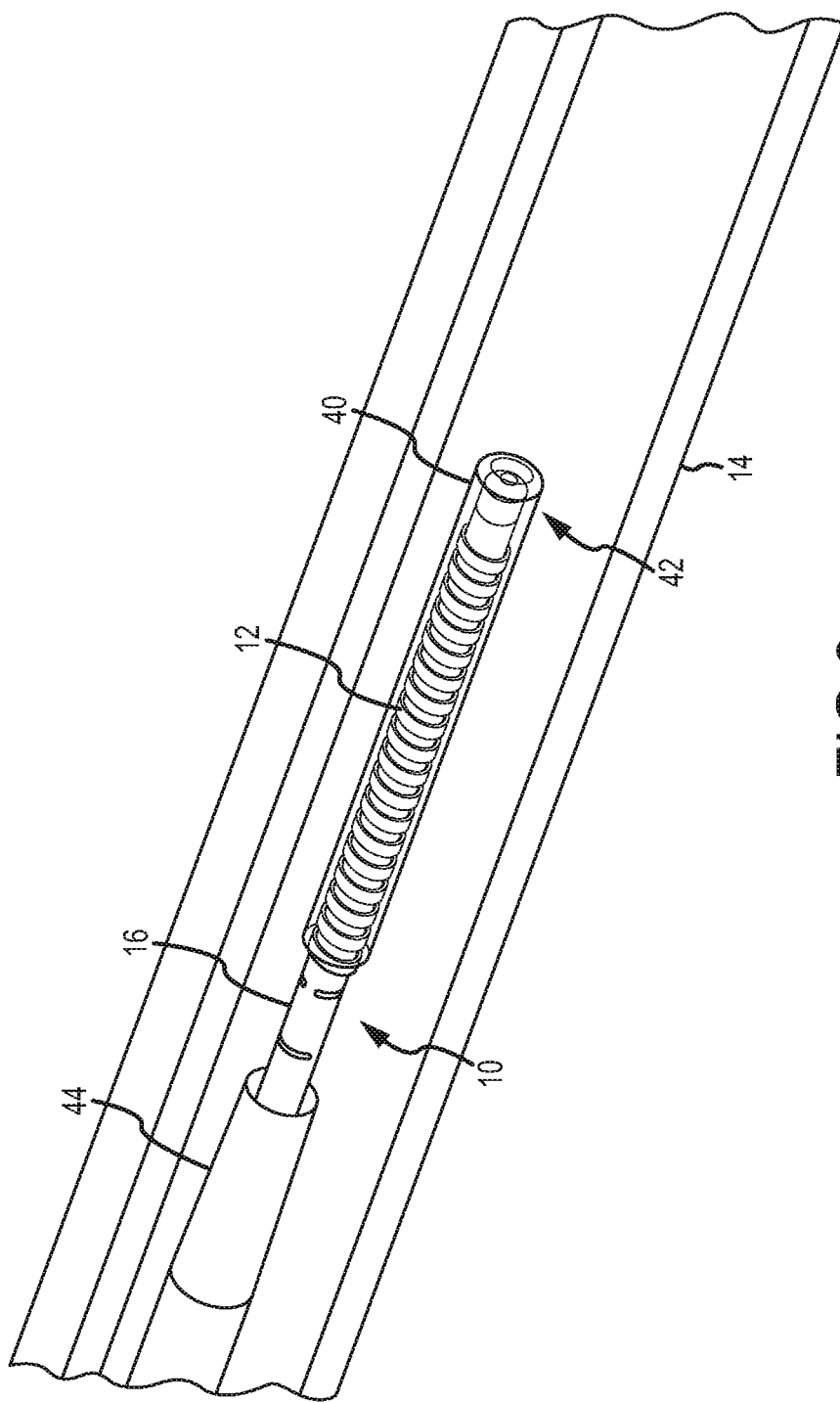
FIG. 9 illustrates an example of a device for reducing or stopping flow through a luminal structure in a patient, having a carrier member, with an expandable member fitting in a first notch and a second notch of the carrier member, and having an occlusion membrane positioned thereabout, positioned in the luminal structure, and extending from a catheter, in accordance with various embodiments of the subject technology.
Figure 10:
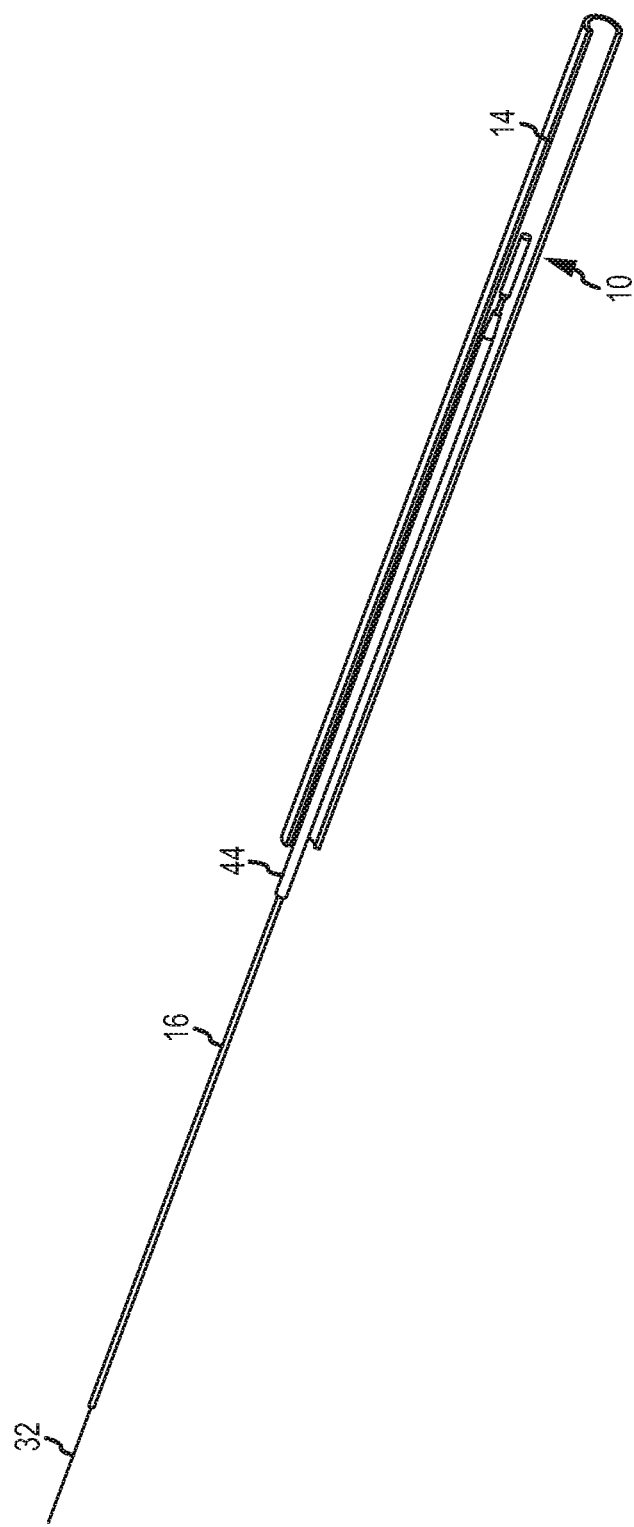
FIG. 10 illustrates an example of a device for reducing or stopping flow through a luminal structure in a patient, positioned in the luminal structure, and extending from a catheter in the luminal structure, in accordance with various embodiments of the subject technology.

FIGS. 9 and 10 illustrate an example of device 10 in a position for expansion, engagement, and release, in accordance with various embodiments of the subject technology. Before being released from catheter 44, expandable member 12 is coiled around carrier member 16. As carrier member 16 and expandable member 12 attached thereto are fed through catheter 44, flouro imaging may provide an indication of the position of carrier member 16. Once the desired position is reached, catheter 44 may be pulled back relative to carrier member 16. In some embodiments, expandable member 12 and occlusion membrane 40 may be deployed from catheter 44 by shifting carrier member 16 distally relative to catheter 44 until expandable member 12 and occlusion membrane 40 extend beyond a distal opening of catheter 44 into luminal structure 14. According to various embodiments of the subject technology, expandable member 12 and occlusion membrane 40 may be accurately deployed and/or repositioned at a deployment site. For example, if an operator of device 10 decides that an initial placement of expandable member 12 and occlusion membrane 40 is undesirable, the operator may redeploy and/or reposition the expandable member 12 and occlusion membrane 40 to another deployment site. In some embodiments, carrier member 16 is configured to shift distally relative to catheter 44 until a portion of expandable member 12 extends beyond a distal opening of catheter 44 into a first deployment site for partially deploying expandable member 12 from catheter 44. Carrier member 16 is configured to shift proximally relative to catheter 44 until the portion of expandable member 12 is retracted proximally into catheter 44 for retracting expandable member 12 into catheter 44. In some embodiments, because a proximal portion of carrier member 16 is still secured to expandable member 12, expandable member 12 is also retracted once carrier member 16 is retracted. Catheter 44 is configured to be positioned within the lumen at a second deployment site for deploying expandable member 12 at the second deployment site. Carrier member 16 is configured to shift distally relative to catheter 44 until expandable member 12 extends beyond the distal opening of catheter 44 into the second deployment site for deploying expandable member 12 from catheter 44 into the second deployment site.

In some embodiments, occlusion membrane 40 may be disposed over distal portion 42 of expandable member 12. According to various embodiments of the subject technology, distal portion 42 and occlusion membrane 40 may extend distally beyond a distal opening of catheter 44 such that when catheter 44 is moved within the lumen to a deployment site, the distally extended portion of occlusion membrane 40 is configured to engage a wall of the lumen to reduce friction and potential vessel injury during device tracking and delivery to the deployment site. Thus, the distally extended portion of occlusion membrane 40 may act as a soft tip when catheter 44 is being navigated through the lumen and/or positioned within the lumen. In such a case, an additional tip may not be necessary. In some embodiments, the distally extended portion of occlusion membrane 40 may be extended about 2 mm beyond the distal opening of catheter 44. In some embodiments, the distally extended portion of occlusion membrane 40 may be extended less than about 2 or greater than about 2 mm beyond the distal opening of catheter 44.

In some embodiments, device 10 further comprises one or more stops disposed between catheter 44 and carrier member 16. In some embodiments, a stop is coupled to an inner surface of catheter 44 and is disposed proximal expandable member 12 when expandable member 12 is positioned between carrier member 16 and catheter 44. Another stop is coupled to an outer surface of carrier member 16 and is disposed proximal the first stop. In some embodiments, when carrier member 16 is shifted distally relative to catheter 44 for deploying expandable member 12, the first stop engages the second stop to substantially prevent carrier member 16 from further distal shifting relative to catheter 44.

Once expandable member 12 is positioned and exposed at the deployment site, it may be expanded to engage luminal structure 14. First portion 34 of expandable member 12 may be released from engagement with carrier member 16 by shifting elongate member 32 distally relative to carrier member 16. Such movement moves elongate member 32 out of first notch 30, allowing first portion 34 of expandable member 12 to move from first notch 30, allowing expandable member 12 to expand radially and at least partially engage luminal structure 14.

Figure 11:
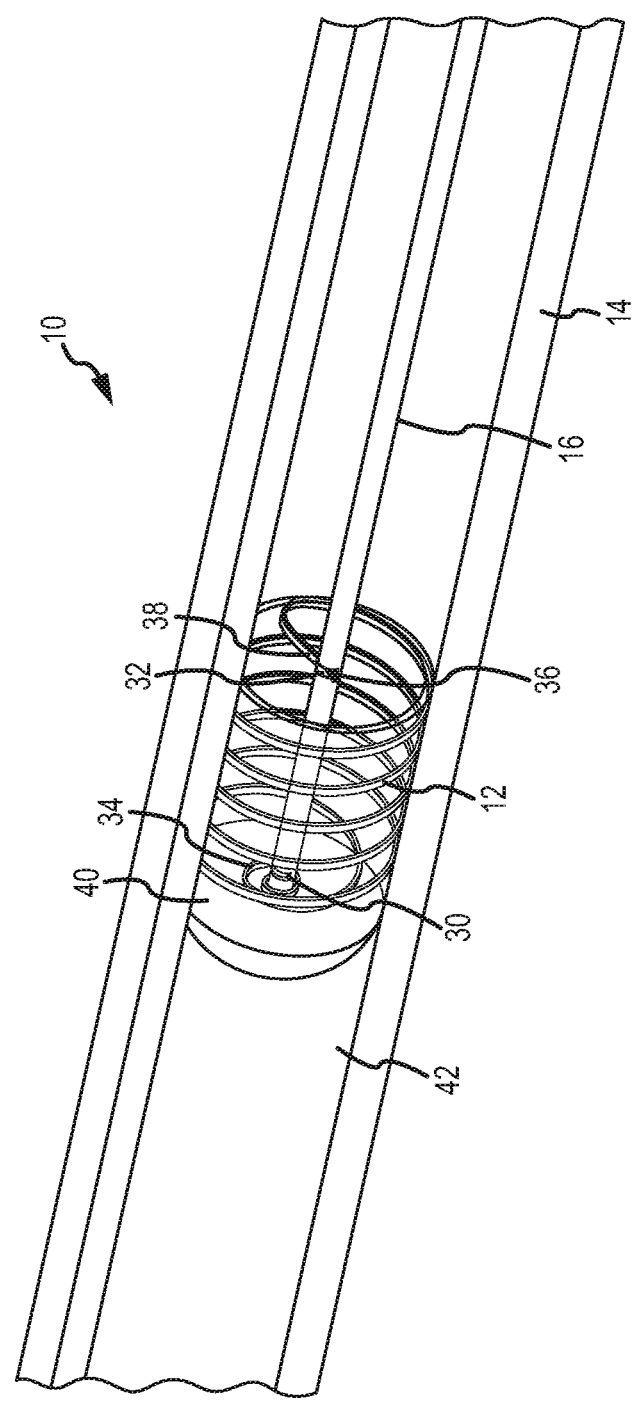
FIG. 11 illustrates an example of a device for reducing or stopping flow through a luminal structure in a patient, expanded in the luminal structure, in accordance with various embodiments of the subject technology.

FIG. 11 illustrates an example of device 10 in an at least partially expanded position ready for release, in accordance with various embodiments of the subject technology. When first portion 34 of expandable member 12 has been released, expandable member 12 and occlusion membrane 40 may remain secured to carrier member 16 until released. At this point, device 10 can be safely removed and pulled back into catheter 44. If full deployment is desired, second portion 38 of expandable member 12 may be released from engagement with carrier member 16 by shifting elongate member 32 distally relative to carrier member 16. Such movement moves elongate member 32 out of second notch 36, allowing second portion 38 of expandable member 12 to move from second notch 36, allowing expandable member 12 to disengage or release from carrier member 16 completely.

Figure 12:
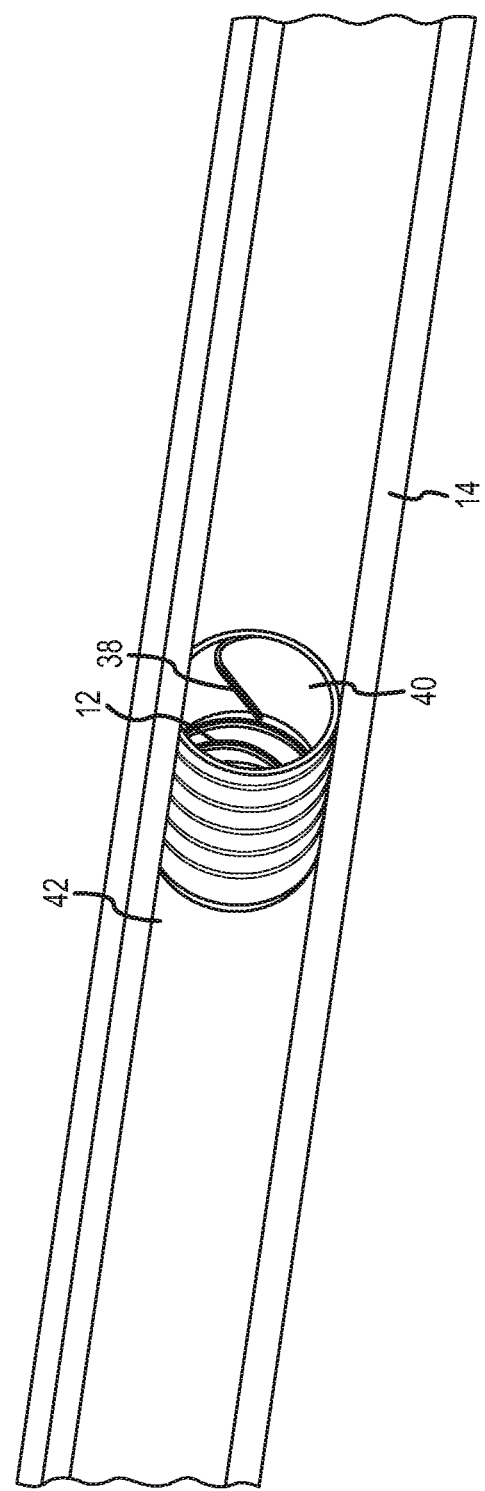
FIG. 12 illustrates an example of a device for reducing or stopping flow through a luminal structure in a patient, expanded within and engaging the luminal structure, with a carrier member removed, in accordance with various embodiments of the subject technology.

FIG. 12 illustrates an example of expandable member 12 and occlusion membrane 40 in place in luminal structure 14, in accordance with various embodiments of the subject technology. Once carrier member 16 is disengaged from expandable member 12, it can me removed from luminal structure 14, leaving expandable member 12 and occlusion membrane 40 in place.

Figure 13:
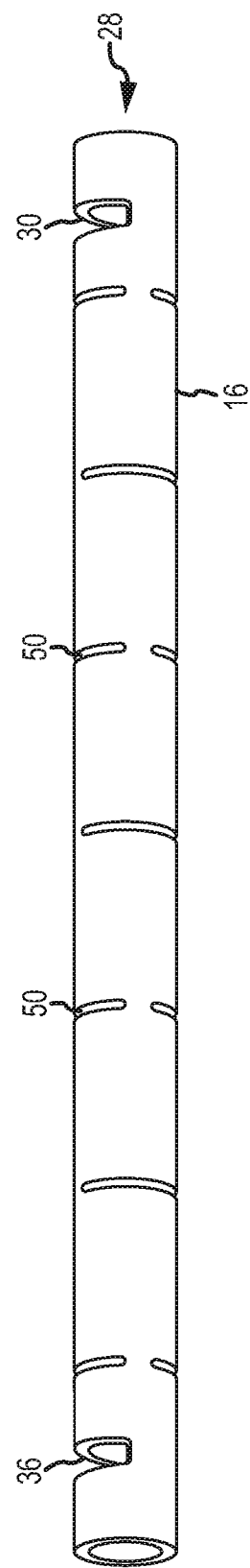
FIG. 13 illustrates an example of a carrier member having slots, in accordance with various embodiments of the subject technology.

FIG. 13 illustrates an example of carrier member 16 having slots 50, in accordance with various embodiments of the subject technology. Slots 50 may enhance flexibility for better tracking device 10 through tortuous anatomy, while maintaining suitable strength. According to various embodiments of the subject technology, carrier member 16 may have at least two slots 50 formed in carrier member 16 by laser cutting or any other mechanical method.

Figure 14:
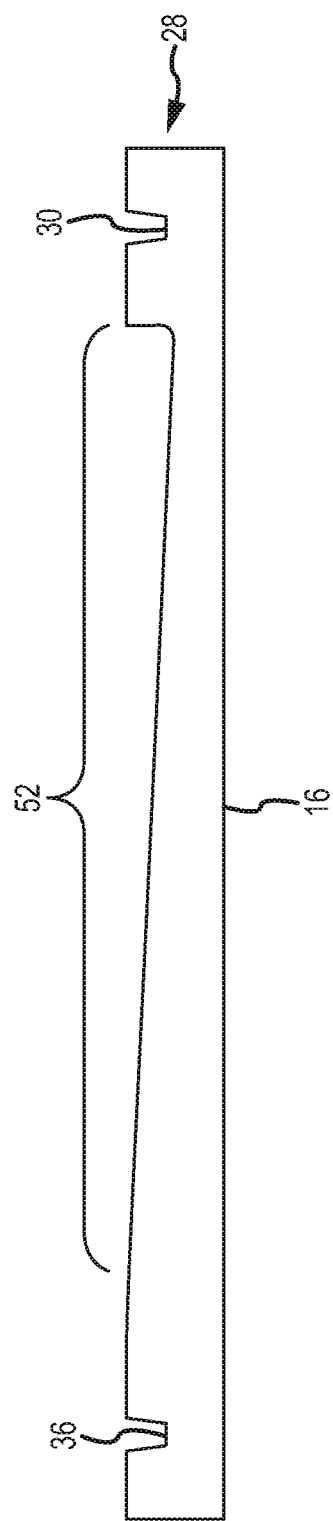
FIG. 14 illustrates an example of a carrier member having a tapered cut, in accordance with various embodiments of the subject technology.

FIG. 14 illustrates an example of carrier member 16 having tapered cut 52, in accordance with various embodiments of the subject technology. Tapered cut 52 may enhance flexibility for better tracking device 10 through tortuous anatomy, while maintaining suitable strength. Tapered cut 52, as an example may have dimensions from an exemplary full circle of 0.40" down to 0.20" at a distal edge. Thus, tapered cut 52 may have a "c" or half-moon shaped cross section. In addition to slots 50 or tapered cut 52, a system of holes drilled in a portion of carrier member 16 may provide flexibility.

Figure 15:
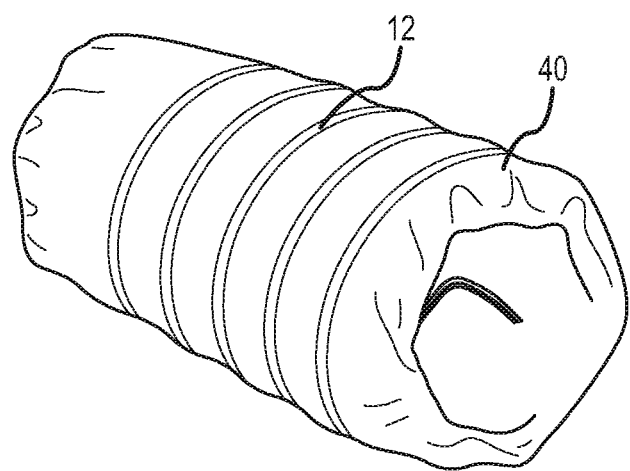
FIG. 15 illustrates an example of a device having an expandable member covered by an occlusion membrane, in accordance with various embodiments of the subject technology.
Figure 16:
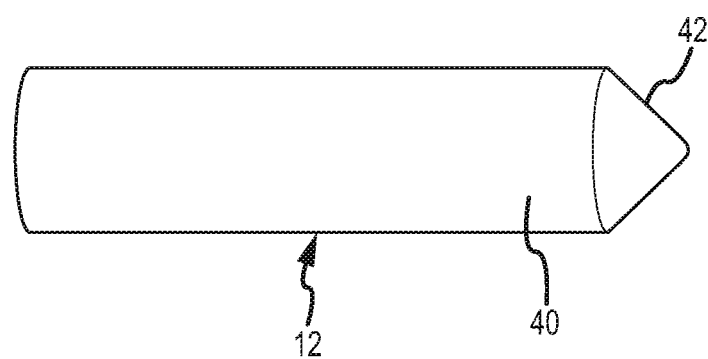
FIG. 16 illustrates an example of a device having an expandable member covered by an occlusion membrane, in accordance with various embodiments of the subject technology.

FIGS. 15 and 16 illustrate examples of expandable member 12, with occlusion membrane 40 thereon, in accordance with various embodiments of the subject technology.

Figure 17:
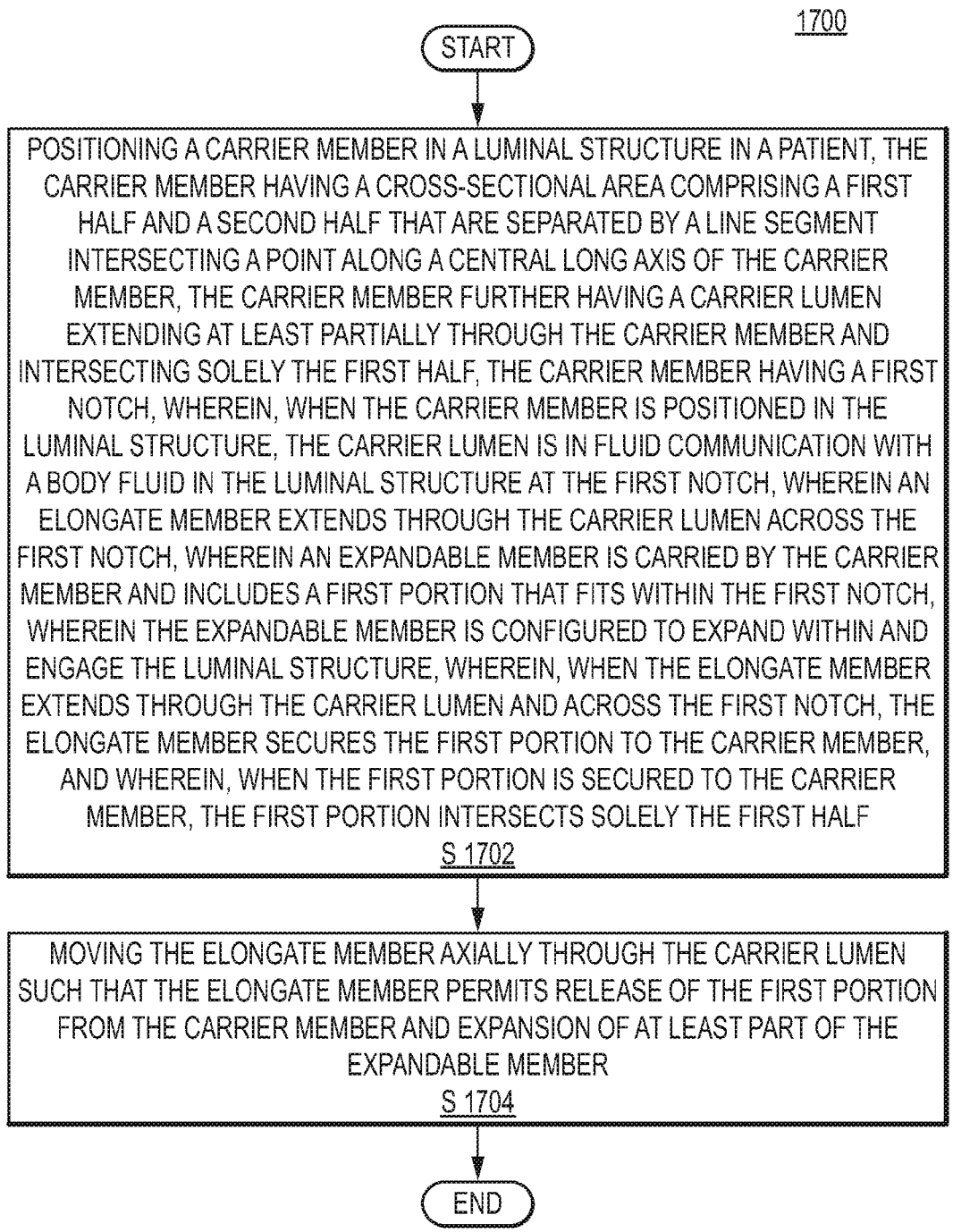
FIG. 17 illustrates an example of a method for reducing or stopping flow through a luminal structure in a patient, in accordance with various embodiments of the subject technology.

FIG. 17 illustrates an example of method 1700 for delivering an expandable member to a luminal structure in a patient, in accordance with various embodiments of the subject technology. Method 1700 comprises positioning a carrier member in a luminal structure in a patient (S1702). The carrier member has a cross-sectional area having a first half and a second half that are separated by a line segment intersecting a point along a central long axis of the carrier member. The carrier member has a carrier lumen extending at least partially through the carrier member and intersecting solely the first half of the cross-sectional area. The carrier member has a first notch such that when the carrier member is positioned in the luminal structure, the carrier lumen is in fluid communication with a body fluid in the luminal structure at the first notch. An elongate member extends through the carrier lumen across the first notch. An expandable member is carried by the carrier member and includes a first portion that fits within the first notch. The expandable member is configured to expand within and engage the luminal structure such that when the elongate member extends through the carrier lumen and across the first notch, the elongate member secures the first portion to the carrier member. When the first portion is secured to the carrier member, the first portion intersects solely the first half. Method 1700 also comprises moving the elongate member axially through the carrier lumen such that the elongate member permits release of the first portion from the carrier member and expansion of at least part of the expandable member (S1704). According to various embodiments, the moving may comprise retracting the elongate member by an operator who is performing the retracting. According to various embodiments, method 1700 may further comprise moving the carrier member through a catheter when positioning the carrier member within the luminal structure.

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

There may be many other ways to implement the invention. Various functions and elements described herein may be partitioned differently from those shown without departing from the scope of the invention. Various modifications to these configurations will be readily apparent to those skilled in the art, and generic principles defined herein may be applied to other configurations. Thus, many changes and modifications may be made to the invention, by one having ordinary skill in the art, without departing from the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A device, for delivering an expandable member to a luminal structure in a patient, comprising:
    a carrier member, positionable in a luminal structure in a patient, having a a carrier lumen extending along a central axis of the carrier member;
    a first notch in the carrier member, wherein, when the carrier member is positioned in the luminal structure, the carrier lumen in fluid communication with a body fluid in the luminal structure at the first notch;
    an elongate member that extends through the carrier lumen and across the first notch; and
    an expandable member carried by the carrier member and configured to expand within and engage the luminal structure, the expandable member having a first portion that fits within the first notch in an engaged configuration;
    wherein in the engaged configuration, (i) the first portion passes from a first end of the first notch through a space between the central axis and the elongate member, (ii) the expandable member terminates in the first portion outside of the first notch, beyond a second end of the first notch, and (iii) the elongate member secures the first portion to the carrier member without being positioned between the expandable member and the central axis within a longitudinal extent of the first notch along the central axis.

2. The device of claim 1, wherein the elongate member is configured to be retracted by an operator such that the elongate member permits the release of the first portion.

3. The device of claim 1, wherein the elongate member permits the release of the first portion when the elongate member does not fully extend across the first notch.

4. The device of claim 1, further comprising a second notch in the carrier member;
    wherein, when the carrier member is positioned in the luminal structure, the carrier lumen is in fluid communication with a body fluid in the luminal structure at the second notch;
    wherein the elongate member extends through the carrier lumen and across the second notch;
    wherein the expandable member comprises a second portion that fits within the second notch;
    wherein, (i) the second portion passes from a first end of the second notch through a space between the central axis and the elongate member, (ii) the expandable member terminates in the second portion outside of the first notch, beyond a second end of the second notch, and (iii) the elongate member secures the second portion to the carrier member without being positioned between the expandable member and the central axis within a longitudinal extent of the second notch along the central axis; and
    wherein the elongate member is configured to move longitudinally through the carrier lumen, after the first portion is released from the carrier member, to release the second portion from the carrier member and release of the expandable member from the carrier member.

5. The device of claim 4, wherein the carrier member has a cross-sectional area comprising a first half and a second half that are separated by a line segment intersecting a point along the central axis of the carrier member, and wherein, when the second portion is secured to the carrier member, the second portion intersects solely the first half.

6. The device of claim 1, wherein the elongate member comprises a wire.

7. The device of claim 1, wherein the expandable member is coiled around the carrier member before being released from the carrier member.

8. The device of claim 1, wherein the carrier member has a cross-sectional area comprising a first half and a second half that are separated by a line segment intersecting a point along the central axis of the carrier member, and wherein the carrier lumen intersects solely the first half.

9. The device of claim 8, wherein, when the first portion is secured to the carrier member, the first portion intersects solely the first half.

10. The device of claim 1, wherein the expandable member is self-expandable such that the first portion is biased in a direction away from the first notch and when the first portion is released by longitudinal movement of the elongate member, the first portion springs out of the first notch.

11. The device of claim 10, wherein the first portion extends from a helical body of the expandable member, the first portion and the helical body being a single, continuous piece of material.

12. The device of claim 11, wherein the first portion comprises a flattened portion of the helical body.

13. The device of claim 1, wherein the first portion is substantially straight.

14. The device of claim 1, wherein the elongate member is configured to move longitudinally through the carrier lumen to release the first portion from the carrier member such that release of the first portion is permitted solely through longitudinal movement of the elongate member.

15. A method, for delivering an expandable member to a luminal structure in a patient, comprising:
    positioning a carrier member in a luminal structure in a patient, the carrier member having a carrier lumen extending along a central axis of the carrier member, the carrier member having a first notch, wherein, when the carrier member is positioned in the luminal structure, the carrier lumen is in fluid communication with a body fluid in the luminal structure at the first notch, wherein an elongate member extends through the carrier lumen across the first notch, wherein an expandable member is carried by the carrier member and includes a first portion that fits within the first notch, wherein the expandable member is configured to expand within and engage the luminal structure, wherein (i) the first portion passes from a first end of the first notch through a space between the central axis and the elongate member, (ii) the expandable member terminates in the first portion outside of the first notch, beyond a second end of the first notch, and (iii) the elongate member secures the first portion to the carrier member without being positioned between the expandable member and the central axis within a longitudinal extent of the first notch along the central axis; and moving the elongate member longitudinally through the carrier lumen to release the first portion from the carrier member.

16. The method of claim 15, wherein the moving comprises proximally retracting the elongate member.

17. The method of claim 15,
wherein the carrier member further comprises a second notch;
wherein, when the carrier member is positioned in the luminal structure, the carrier lumen is in fluid communication with a body fluid in the luminal structure at the second notch;
wherein the elongate member extends through the carrier lumen across the second notch;
wherein the expandable member comprises a second portion that fits within the second notch;
wherein, (i) the second portion passes from a first end of the second notch through a space between the central axis and the elongate member, (ii) the expandable member terminates in the second portion outside of the first notch, beyond a second end of the second notch, and (iii) the elongate member secures the second portion to the carrier member without being positioned between the expandable member and the central axis within a longitudinal extent of the second notch along the central axis; and
wherein the method further comprises moving, after the first portion is released from the carrier member, the elongate member longitudinally through the carrier lumen to release the second portion from the carrier member and release of the expandable member from the carrier member.

18. The method of claim 17, wherein the moving comprises proximally retracting the elongate member to release the first and second ends from the carrier member.

19. The method of claim 15, wherein the carrier member has a cross-sectional area comprising a first half and a second half that are separated by a line segment intersecting a point along the central axis of the carrier member, and wherein the carrier lumen intersects solely the first half.

20. The method of claim 19, wherein, when the first portion is secured to the carrier member, the first portion intersects solely the first half.

21. The method of claim 15, wherein before the moving, the first portion exerts a radial force against the elongate member in a direction radially away from the first notch, such that the moving permits the first portion to spring out of the first notch.

22. The method of claim 21, wherein the first portion extends from a helical body of the expandable member, the first portion and the helical body being a single, continuous piece of material.

23. The method of claim 22, wherein the first portion comprises a flattened portion of the helical body.

24. The method of claim 15, wherein the first portion is substantially straight.

25. The method of claim 15, wherein the moving comprises moving the elongate member longitudinally through the carrier lumen to release the first portion from the carrier member such that release of the first portion is permitted solely through longitudinal movement of the elongate member.

26. A device, for delivering an expandable member to a luminal structure in a patient, comprising:
a carrier member having a lumen extending along a central axis of the carrier member and a notch extending through the carrier member into the lumen;
a self-expandable member positioned around the carrier member and terminating in a portion that fits within the notch and extends into and out of the notch; and
a wire longitudinally movable through the carrier member lumen and positionable across the notch to secure the portion to the carrier member without being positioned between the expandable member and the central axis within a longitudinal extent of the notch along the central axis.

27. The device of claim 26, wherein the portion is biased in a direction away from the notch such that when the portion is released by longitudinal movement of the wire, the portion springs out of the notch.

28. The device of claim 27, wherein the portion extends from a helical body of the expandable member, the portion and the helical body being a single, continuous piece of material.

29. The device of claim 28, wherein the portion comprises a flattened section of the helical body.

30. The device of claim 26, wherein the lumen comprises first and second halves that are separated by a line segment intersecting a point along a central long axis of the carrier member, wherein the wire extends across the notch within only the first half.

31. The device of claim 26, wherein the carrier member comprises a second notch extending through the carrier member into the lumen, wherein a second portion of the expandable member fits within the second notch to be secured to the carrier member.

32. The device of claim 31, further comprising a second wire longitudinally moveable through the carrier member, wherein the second wire is longitudinally movable across the second notch to secure the second portion to the carrier member.

33. The device of claim 26, wherein the portion is substantially straight.

34. The device of claim 26, wherein release of the portion is permitted solely through longitudinal disengagement of the wire with the portion.

* * * * *